US011660436B1

(12) United States Patent
Kam et al.

(10) Patent No.: US 11,660,436 B1
(45) Date of Patent: May 30, 2023

(54) DEVICE, SYSTEM, AND FORMULATION FOR ORAL DELIVERY OF FUNCTIONALIZED PARTICLES

(71) Applicant: Verily Life Sciences LLC, South San Francisco, CA (US)

(72) Inventors: Kimberly Kam, Orinda, CA (US); Janet Ayako Tamada, Mountain View, CA (US); Vasiliki Demas, San Francisco, CA (US); Miguel Diaz Moreno, Boston, MA (US)

(73) Assignee: Verily Life Sciences LLC, South San Francisco, CA (US)

( * ) Notice: Subject to any disclaimer, the term of this patent is extended or adjusted under 35 U.S.C. 154(b) by 397 days.

(21) Appl. No.: 16/929,563

(22) Filed: Jul. 15, 2020

Related U.S. Application Data

(62) Division of application No. 15/223,156, filed on Jul. 29, 2016, now abandoned.
(Continued)

(51) Int. Cl.
*A61M 31/00* (2006.01)
*A61B 5/145* (2006.01)

(52) U.S. Cl.
CPC ....... *A61M 31/002* (2013.01); *A61B 5/14546* (2013.01); *A61M 31/005* (2013.01); *A61M 2205/0255* (2013.01); *A61M 2205/04* (2013.01)

(58) Field of Classification Search
CPC ........ A61M 31/002; A61M 2205/0255; A61M 2205/04; A61B 5/14546
See application file for complete search history.

(56) References Cited

U.S. PATENT DOCUMENTS

| 5,651,979 A * | 7/1997 | Ron | A61L 31/145 604/892.1 |
|---|---|---|---|
| 6,256,522 B1 | 7/2001 | Schultz | |

(Continued)

FOREIGN PATENT DOCUMENTS

WO 2013027182 2/2013

OTHER PUBLICATIONS

U.S. Appl. No. 15/223,156, "Advisory Action", dated Nov. 22, 2019, 3 pages.
(Continued)

*Primary Examiner* — Bradley J Osinski
(74) *Attorney, Agent, or Firm* — Kilpatrick Townsend & Stockton LLP

(57) ABSTRACT

A device includes a capsule sized to pass through a lumen of a gastrointestinal tract; an enteric coating surround at least a portion of the capsule and configured to protect the capsule form stomach acid while allowing degradation of the capsule in the small intestine of the gastrointestinal tract; a plurality of functionalized particles disposed within the capsule, a plurality of tissue penetrating members configured to puncture a wall of the lumen of the intestinal tract; and an actuator having a first configuration and a second configuration. The actuator is configured to retain the plurality of functionalized particles within the capsule in the first configuration. The actuator is further configured to advance the plurality of functionalized particles from the capsule into a wall of the lumen of the gastrointestinal tract via the plurality of tissue penetrating members by the actuator transitioning from the first configuration to the second configuration.

10 Claims, 19 Drawing Sheets

Related U.S. Application Data

(60) Provisional application No. 62/200,882, filed on Aug. 4, 2015.

(56) References Cited

U.S. PATENT DOCUMENTS

| | | | |
|---|---|---|---|
| RE38,525 E | 6/2004 | Stanley et al. | |
| 7,214,190 B1 | 5/2007 | Wilson | |
| 7,236,812 B1 | 6/2007 | Ballerstadt et al. | |
| 7,699,834 B2 | 4/2010 | Hood et al. | |
| 7,701,580 B2 | 4/2010 | Bassler et al. | |
| 7,763,856 B2 | 7/2010 | Kiesel et al. | |
| 7,817,254 B2 | 10/2010 | Hegyi et al. | |
| 7,817,276 B2 | 10/2010 | Kiesel et al. | |
| 7,844,314 B2 | 11/2010 | Al-Ali | |
| 7,894,068 B2 | 2/2011 | Bassler et al. | |
| 8,153,949 B2 | 4/2012 | Kiesel et al. | |
| 8,323,188 B2 | 12/2012 | Tran | |
| 8,344,731 B2 | 1/2013 | Lee | |
| 8,368,402 B2 | 2/2013 | Lee et al. | |
| 8,721,620 B2 * | 5/2014 | Imran | A61P 5/18 604/60 |
| 8,734,429 B2 | 5/2014 | Imran et al. | |
| 9,415,004 B2 | 8/2016 | Imran | |
| 9,757,514 B2 | 9/2017 | Imran et al. | |
| 2004/0253304 A1 | 12/2004 | Gross et al. | |
| 2004/0259270 A1 | 12/2004 | Wolf | |
| 2005/0054907 A1 | 3/2005 | Page et al. | |
| 2005/0058701 A1 | 3/2005 | Gross et al. | |
| 2007/0255122 A1 | 11/2007 | Vol et al. | |
| 2008/0255543 A1 | 10/2008 | Tanaka et al. | |
| 2009/0030473 A1 | 1/2009 | Khawaled et al. | |
| 2010/0021536 A1 | 1/2010 | Gross | |
| 2010/0049010 A1 | 2/2010 | Goldreich | |
| 2010/0222642 A1 | 9/2010 | Trovato | |
| 2010/0303723 A1 * | 12/2010 | Farokhzad | A61K 47/6937 424/85.4 |
| 2011/0028803 A1 | 2/2011 | Ollmar | |
| 2011/0117028 A1 | 5/2011 | Zharov | |
| 2011/0160129 A1 | 6/2011 | Imran | |
| 2011/0160699 A1 | 6/2011 | Imran | |
| 2012/0010590 A1 | 1/2012 | Imran | |
| 2012/0027855 A1 * | 2/2012 | Deshmukh | A61K 9/4808 424/465 |
| 2013/0039848 A1 | 2/2013 | Bradbury et al. | |
| 2013/0164373 A1 | 6/2013 | Imran | |
| 2013/0165859 A1 | 6/2013 | Imran | |
| 2015/0064241 A1 | 3/2015 | Conrad | |

OTHER PUBLICATIONS

U.S. Appl. No. 15/223,156, "Final Office Action", dated Aug. 2, 2019, 17 pages.

U.S. Appl. No. 15/223,156, "Non Final Office Action", dated Jul. 25, 2018, 13 pages.

U.S. Appl. No. 15/223,156, "Non-Final Office Action", dated Jan. 24, 2020, 13 pages.

U.S. Appl. No. 15/223,156, "Non-Final Office Action", dated Jan. 29, 2019, 16 pages.

Arruebo et al., "Antibody-Conjugated Nanoparticles for Biomedical Applications", Journal of Nanomaterials, vol. 2009, Article ID 439389, 2009, 24 pages.

Chaturvedi et al., "A Review on Mucoadhesive Polymer Used in Nasal Drug Delivery System", Journal of Advanced Pharmaceutical Technology & Research, vol. 2(4), Oct.-Dec. 2011, pp. 215-222.

Liu et al., "Magnetic Resonance Monitoring of Focused Ultrasound/ Magnetic Nanoparticle Targeting Delivery of Therapeutic Agents to the Brain", PNAS Early Edition, vol. 107, No. 34, 2010, pp. 15205-15210.

Shao et al., "Magnetic Nanoparticles for Biomedical NMR-based Diagnostics", Beilstein Journal of Nanotechnology, 2010, pp. 142-154.

* cited by examiner

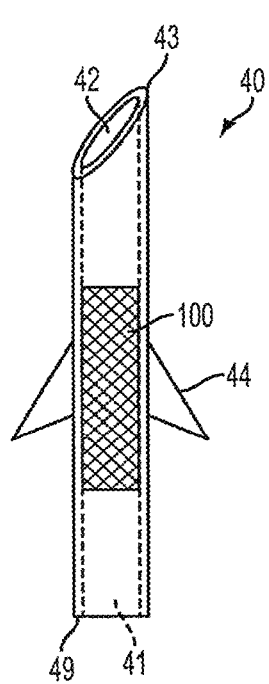 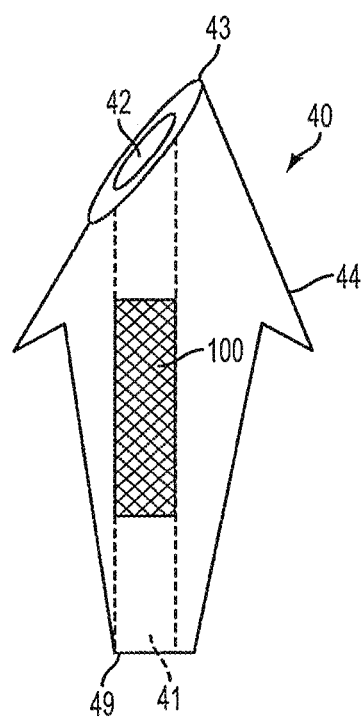
FIG. 2A  FIG. 2B
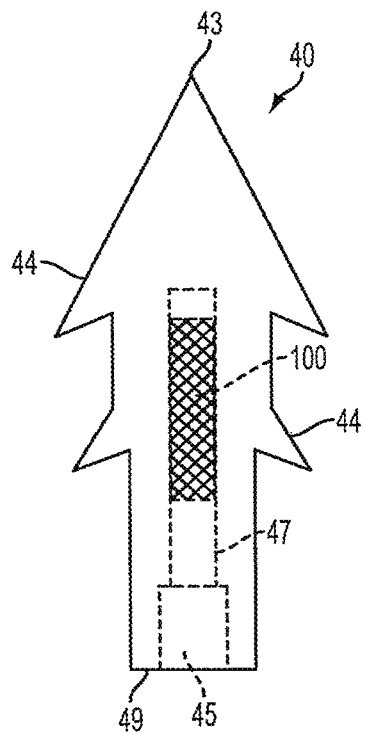 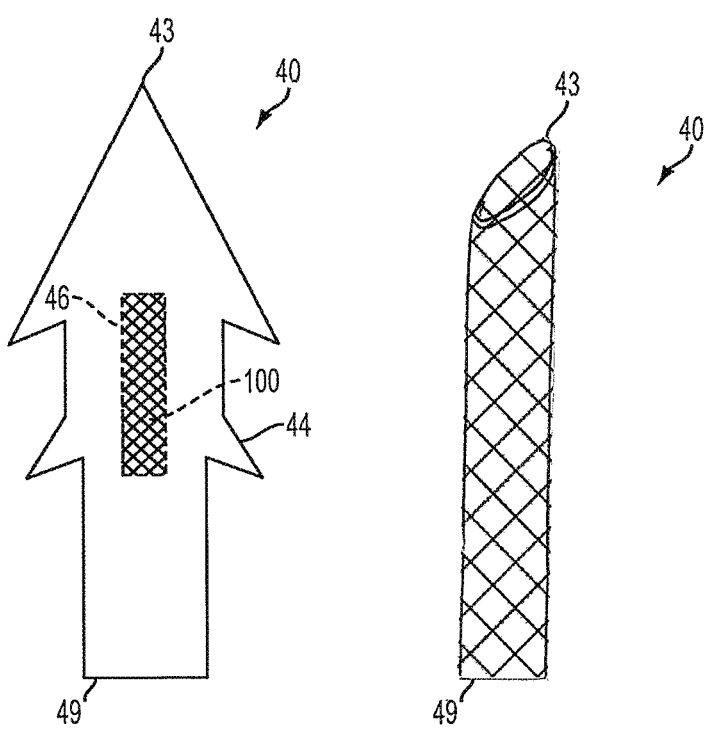
FIG. 2C  FIG. 2D  FIG. 2E

DEVICE, SYSTEM, AND FORMULATION FOR ORAL DELIVERY OF FUNCTIONALIZED PARTICLES

CROSS-REFERENCE

The present application is a divisional of U.S. patent application Ser. No. 15/223,156, filed on Jul. 29, 2016, which claims priority to and filing benefit of U.S. Provisional Patent Application No. 62/200,882, filed Aug. 4, 2015, which are incorporated by reference in their entireties.

BACKGROUND

Unless otherwise indicated herein, the materials described in this section are not prior art to the claims in this application and are not admitted to be prior art by inclusion in this section.

A number of scientific methods have been developed in the medical field to evaluate physiological conditions of a person by detecting and/or measuring one or more analytes in a person's blood or other bodily fluids. The one or more analytes could be any analytes that, when present in or absent from the blood, or present at a particular concentration or range of concentrations, may be indicative of a medical condition or health state of the person. The one or more analytes could include enzymes, reagents, hormones, proteins, cells or other molecules, such as carbohydrates, e.g., glucose.

In a typical scenario, a person's blood is drawn and either sent to a lab or input into a handheld testing device, such as a glucose meter, where one or more tests are performed to measure various analyte levels and parameters in the blood. For most people, the blood tests are infrequent, and an abnormal analyte level indicative of a medical condition may not be identified until the next blood test is performed. Even in the case of relatively frequent blood testing, such as may be found with those with diabetes, who regularly draw blood to test for blood glucose concentration, those blood tests are typically performed when the user is awake, although the blood glucose levels (and potential variations in such levels) occurring during the night could provide important information to assist a physician in assessing that person's medical condition. Further, most known methods of analyte detection and analysis require the collection of blood or other bodily fluid samples, which may be inconvenient, invasive and require significant patient compliance.

Methods for introduction of imaging, therapeutic or medicinal agents into the body, for the treatment or analysis of medical conditions include oral, intravenous, intramuscular, subcutaneous, transmucosal and topical delivery. Some of these methods may not be applicable for the delivery of all agents or substances. For example, some proteins, antibodies, peptides, vaccines and gene-based drugs cannot be given via traditional oral delivery methods due to a number of reasons, including: poor oral toleration, with complications including gastric irritation and bleeding; breakdown/degradation of the drug compounds in the stomach; and poor, slow, erratic or inefficient absorption of the drug due to molecular size and charge issues. Conventional alternative drug delivery methods such as intravenous and intramuscular delivery have a number of drawbacks including pain and risk of infection from a needle stick, requirements for the use of sterile technique and the requirement and associated risks of maintaining an IV line in a patient for an extended period of time. While other drug delivery approaches have been employed such as implantable drug delivery pumps, these approaches require the semi-permanent implantation of a device and can still have many of the limitations of IV delivery.

SUMMARY

In one aspect of the present disclosure, a device is provided. The device includes: a (a) capsule sized to pass through a lumen of a gastrointestinal tract; (b) an enteric coating surrounding at least a portion of the capsule, the enteric coating configured to protect the capsule from stomach acid while allowing for degradation of the capsule in a target portion of the gastrointestinal tract; (c) a plurality of tissue penetrating members arranged within the capsule and configured to puncture a wall of the target portion of the gastrointestinal tract, the tissue penetrating members comprising at least one type of functionalized particles; and (d) an actuator having a first configuration and a second configuration, wherein the actuator is configured to retain the plurality of tissue penetrating members within the capsule in the first configuration, and wherein the actuator is configured to advance the at least one type of functionalized particles into or across a wall of the lumen of the target portion of the gastrointestinal tract via the plurality of tissue penetrating members by the actuator transitioning from the first configuration to the second configuration.

In another aspect of the present disclosure, a system is provided. The system includes: (a) a swallowable device comprising: a capsule sized to pass through a lumen of a gastrointestinal tract; an enteric coating surrounding at least a portion of the capsule, the enteric coating configured to protect the capsule from stomach acid while allowing for degradation of the capsule in a target portion of the gastrointestinal tract; a plurality of tissue penetrating members arranged within the capsule and configured to puncture a wall of the lumen of the target portion of the gastrointestinal tract, the tissue penetrating members comprising at least one type of functionalized particles; an actuator having a first configuration and a second configuration, wherein the actuator is configured to retain the plurality of tissue penetrating members within the capsule in the first configuration, and wherein the actuator is configured to advance the at least one type of functionalized particles into or across a wall of the lumen of the target portion of the gastrointestinal tract via the plurality of tissue penetrating members by the actuator transitioning from the first configuration to the second configuration; and (b) a detector configured to detect an analyte response signal related to interaction of one or more target analytes with the functionalized particles.

In another aspect of the present disclosure, an orally administrable composition is provided. The orally administrable composition includes a core comprising a mucoadhesive material and at least one type of functionalized particles, wherein the least one type of functionalized particles is labeled with an active transport ligand and wherein the mucoadhesive material is configured to adhere to a wall of the gastrointestinal tract; an excipient surrounding at least a portion of the core; and an enteric coating surrounding the excipient and the core, wherein the enteric coating configured to protect the core from stomach acid while allowing for degradation of the core in a target portion of the gastrointestinal tract.

In another aspect, a method is provided. The method includes the steps of: (a) orally administering to a mammal a capsule sized to pass through a lumen of a gastrointestinal tract; an enteric coating surrounding at least a portion of the capsule, the enteric coating configured to protect the capsule from stomach acid while allowing for degradation of the capsule in a target portion of the gastrointestinal tract; a plurality of tissue penetrating members arranged within the capsule and configured to puncture a wall of the lumen of the target portion of the gastrointestinal tract, the tissue penetrating members comprising at least one type of functionalized particles; and an actuator having a first configuration and a second configuration, wherein the actuator is configured to retain the plurality of tissue penetrating members within the capsule in the first configuration, and wherein the actuator is configured to advance the at least one type of functionalized particles into or across a wall of the lumen of the target portion of the gastrointestinal tract via the plurality of tissue penetrating members by the actuator transitioning from the first configuration to the second configuration, wherein functionalized particles configured to bind to selected markers of tumor cells or tissue or components or analytes in blood; (b) waiting a time sufficient to allow the functionalized particles to bind to the selected markers of the tumor cells or tissue; and c) imaging the cells or tissue with a non-invasive imaging technique that has a resolution enhanced by the presence of the functionalized particles on or within the cells or tissue.

In another aspect, a further method is provided. The method includes the steps of: (a) orally administering to a mammal a composition comprising a core comprising a mucoadhesive material and at least one type of functionalized particles, wherein the least one type of functionalized particles is labeled with an active transport ligand and wherein the mucoadhesive material is configured to adhere to a wall of the gastrointestinal tract; an excipient surrounding at least a portion of the core; and an enteric coating surrounding the excipient and the core, wherein the enteric coating configured to protect the core from stomach acid while allowing for degradation of the core in a target portion of the gastrointestinal tract, wherein functionalized particles configured to bind to selected markers of tumor cells or tissue; (b) waiting a time sufficient to allow the functionalized particles to bind to the selected markers of the tumor cells or tissue; and (c) imaging the cells or tissue with a non-invasive imaging technique that has a resolution enhanced by the presence of the functionalized particles on or within the cells or tissue.

In another aspect of the present disclosure, a system is provided. The system includes: (a) an orally administrable composition comprising a core comprising a mucoadhesive material and at least one type of functionalized particles, wherein the least one type of functionalized particles is labeled with an active transport ligand and wherein the mucoadhesive material is configured to adhere to a wall of the gastrointestinal tract; an excipient surrounding at least a portion of the core; and an enteric coating surrounding the excipient and the core, wherein the enteric coating configured to protect the core from stomach acid while allowing for degradation of the core in a target portion of the gastrointestinal tract, wherein functionalized particles configured to bind to selected markers of tumor cells or tissue or components or analytes in blood; and (b) a detector configured to detect an analyte response signal related to interaction of one or more target analytes with the functionalized particles.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIGS. 2A-2E are side views of embodiments of tissue penetrating members for use in a swallowable delivery device.

DETAILED DESCRIPTION

Figure 1:
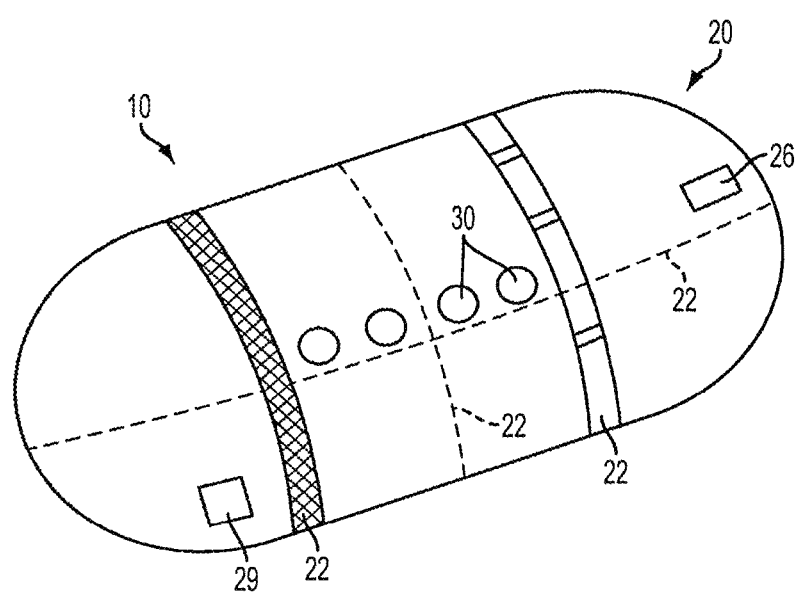
FIG. 1 is a perspective view of an embodiment of a swallowable delivery device.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

Quantitative and qualitative information regarding physiological parameters relating to the health of the person may be obtained by noninvasively measuring, with a wearable device mounted to the body, one or more analytes in blood circulating in subsurface vasculature. The one or more analytes could be any analytes that, when present in the blood at a particular concentration or range of concentrations, may be indicative of a medical condition or health of the person wearing the device. For example, the one or more analytes could include enzymes, hormones, proteins, or other molecules as well as cells such as circulating tumor cells.

In an example embodiment, the wearable device obtains at least some of the health-related information by detecting the binding of a clinically-relevant analyte to functionalized particles, such as nanoparticles or microparticles, introduced into the gastrointestinal tract. The particles may be made of an inert material, such as polystyrene, and can have a diameter that is less than about 20 micrometers. In some embodiments, the particles have a diameter on the order of about 10 nm to 1 µm. In further embodiments, small particles on the order of 10-100 nm in diameter may be assembled to form a larger "clusters" or "assemblies on the order of 1-10 micrometers. Those of skill in the art will understand a "particle" in its broadest sense and that it may take the form of any fabricated material, a molecule, cryptophan, a virus, a phage, etc. Further, a particle may be of any shape, for example, spheres, rods, non-symmetrical shapes, etc. In some examples, the particles may be magnetic and can be formed from a paramagnetic, super-paramagnetic or ferromagnetic material or any other material that responds to a magnetic field.

The particles, or a group of several particles in a complex, may be functionalized with a receptor that has a specific affinity to bind to or interact with a clinically relevant analyte including cells such as tumor cells. The receptor may be inherent to the particle itself. For example, the particle itself may be a virus or a phage with an inherent affinity for certain analytes. Additionally or alternatively, the particles can be functionalized by covalently or otherwise attaching or associating a receptor that specifically binds or otherwise recognizes a particular clinically-relevant analyte. The functionalized receptor can be an antibody, peptide, nucleic acid, phage, bacteria, virus, or any other molecule with a defined affinity for a target analyte. Other compounds or molecules, such as fluorophores or autofluorescent or luminescent markers, which may assist in interrogating the particles in vivo, may also be attached to the particles.

The wearable device may further include one or more data collection systems for interrogating, in a noninvasive manner, the functionalized particles present in a lumen of the subsurface vasculature in the local area of the wearable device. In one example, the wearable device includes a detector for detecting a response signal that is transmitted from the portion of subsurface vasculature in response to the interrogating signal. While not necessary in all cases, the wearable device may also include a signal source for transmitting an interrogating signal that can penetrate the wearer's skin into the portion of subsurface vasculature and induce a response signal that is related to the binding of the functionalized particles to the target analyte. The interrogating signal can be any kind of signal that is benign to the wearer and results in a response signal that can be used to detect binding of the clinically-relevant analyte to the functionalized particles.

In addition, the data collected by the wearable device may be analyzed, either locally on or remotely from the wearable device, to detect the presence or absence of the clinically-relevant analyte. In some examples, the data may be analyzed to further determine a concentration of the clinically-relevant analyte based on the response signal detected by the detector and determine whether a medical condition is indicated based on at least the presence, absence and/or concentration of the clinically-relevant analyte. As one possible example for use of the data collected by the wearable device, the presence of an unstable arterial plaque that could potentially cause a heart attack or stroke is often associated with an increase in certain protein markers in the blood. A person who may be at risk for this medical condition may take particles that are functionalized to bind to such protein markers and may wear on his or her wrist a device that is configured to periodically (e.g., every hour) collect and interrogate the functionalized particles to determine the concentrations of the protein markers. If the device determines that the concentrations of the protein markers indicate an elevated risk of a heart attack or other life-threatening episode, the device may generate an alert through the user interface (e.g., an audible alarm) so that the person wearing the device can seek immediate medical attention.

In another embodiment of the invention, a method is provided for in vivo imaging in a mammal of tumor cells or tissue that express a selected marker. The method includes the steps of: (a) orally administering to the mammal a device or composition including functionalized particles configured to bind to selected markers of tumor cells or tissue; (b) waiting a time sufficient to allow the functionalized particles to bind to the selected markers of the tumor cells or tissue; and (c) imaging the cells or tissue with a non-invasive imaging technique that has a resolution enhanced by the presence of the functionalized particles on or within the cells or tissue. The amount of time sufficient to allow the targeting entity to bind can vary from patient to patient as well as the type of tumor cells or tissue that is being imaged and the amount of functionalized particles being administered. In general, the amount of time can range for instance from 30 minutes to 24 hours, one hour to 12 hours, or one hour to three hours, In some embodiments, the imaging technique is selected from the group consisting of magnetic resonance imaging (MRI), magnetic spectroscopy, X-ray, positron emission tomography (PET), computer tomography (CT), photoacoustic imaging, and ultrasonic imaging.

Imaging techniques can non-invasively measure biological functions, evaluate cellular and molecular events, and reveal the inner workings of a body. Examples of imaging techniques include magnetic resonance imaging (MRI), positron emission tomography (PET), x-ray tomography, luminescence and fluorescence (optical imaging), deep tissue Near Infrared (NIR) imaging, ultrasound imaging, and photoacoustic imaging. Each of these techniques can differ from one another in the resolution, sensitivity, and anatomical information they provide about the subject. For example, though optical imaging has high sensitivity, it provides limited anatomical background information, and can display artifacts due to tissue absorbance and scattering. MRI can be used to generate contrast to detect tumors in deep tissue and provide true three dimensional imaging of biological structures and processes at cellular resolution. X-ray contrast is useful to differentiate tissues with small differences in their density.

In certain embodiments, a device or composition having functionalized particles are provided that are useful as imaging (e.g., contrast) agents, and/or therapeutics. In various embodiments the functionalized particles are effective a multiple-modality effectors. That is, they can simultaneously provide one or more imaging modalities, and/or one or more targeting modalities, and/or one or more therapeutic modalities.

In one embodiment, the functionalized particles can be attached to at least one imaging agent (e.g., contrast agents). In some embodiments, the functionalized particles includes two or more different contrast agents so that two or more different imaging techniques can be used. Suitable contrast agents include, but are not limited to magnetic resonance imaging materials, electron spin resonance (ESR) materials, near infrared materials, PET materials, and the like. In some embodiments, the nanoparticle conjugate can itself be a moiety that provides a detectable signal (e.g., a quantum dot) in which case the nanoparticle/agent combination can provide at least two different detection modalities.

In certain embodiments, the functionalized particles can simply be used as detection agents (e.g., as MRI contrast agents). When coupled to a targeting entity they can, for example, be used to detect the presence, and/or location, and/or size of the target (e.g., a tumor cell or tumor mass or tissue) in vivo. In certain embodiments, the functionalized particles are used simply as therapeutic agents that, when coupled to a targeting entity, can be used to deliver a therapeutic moiety to a target cell or tissue. In certain embodiments, the nanoparticle conjugates are used both to image a target cell or tissue and to deliver one or more therapeutic moieties thereto.

In certain embodiments, methods are provided for imaging (e.g., detecting or quantifying the presence or absence, and/or the location and/or the size of a target) a tumor cell and/or tumor tissue. Similarly, in certain embodiments, methods are provided for delivering a therapeutic agent in proximity to, and/or on the surface of, and/or internalized into a tumor cell and/or tissue. In certain embodiments the methods involve using the nanoparticle conjugate to both image a target cell or tissue and to deliver a therapeutic moiety thereto.

The functionalized particles may be introduced into the blood stream, or other bodily fluid, by injection, ingestion, inhalation, transdermally, or in some other manner. In one example, the functionalized particles are delivered to the gastrointestinal (GI) tract by a swallowable delivery device such as a capsule. As used herein, "GI tract" refers to the esophagus (E), stomach (S), small intestine (SI), large intestine (LI) and anus, while "Intestinal tract" refers to the small and large intestine. Various embodiments of the invention can be configured and arranged for delivery of medication 100 into both the intestinal tract as well as the entire GI tract. The capsule includes an interior volume and can be fabricated from various biocompatible polymers known in the art. The capsule can be fabricated from various non-toxic materials including various biodegradable polymers. The capsule can also have an enteric or other coating for protecting the capsule from stomach acids while allowing for biodegradation in the small intestine so as to allow the device to deliver functionalized particles into the wall of the small intestine responsive to pH or other conditions in the small intestine. In one embodiment, a mucoadhesive layer can be present at least on a portion of the surface of the capsule to assist in temporarily or anchoring attaching the capsule to the wall of the of the intestinal tract, e.g., the large intestine. The mucoadhesive layer can be covered by an enteric coating which dissolves in the small intestine, exposing the mucoadhesive layer to the walls of the small intestine.

The delivery device described herein may be used for the delivery of functionalized particles to the gastrointestinal tract of a mammal, such as a human, canine, bovine or porcine intestinal tract. Characteristics of the delivery device and functionalized particles may be tailored for the particular mammal(s) under study. For example, in embodiments of the device employing various biodegradable materials, the pH under which those materials will degrade may be selected based on the pH of the target portion of the gastrointestinal tract of the chosen mammal.

In one embodiment, the capsule includes an expandable member and a tissue penetrating member advanceable into the intestinal wall by expansion of the expandable member. The capsule includes an interior volume and at least one aperture through which the tissue penetrating member can be advanced into the intestinal wall. In some examples, the expandable member is provided as a balloon disposed within the capsule interior volume and coupled to the tissue penetrating member. The balloon can be attached to an interior wall of the capsule in a least a partially non-expanded state and can comprise various non-compliant polymers known in the art such as PET, polyethylene and polyimide. The balloon may be thin walled e.g., less than about 0.02 millimeters.

Expansion of the balloon can occur in response to a chemical, electrical, mechanical or external stimulus. In some embodiments, balloon expansion occurs by filling of the balloon with a gas, which may be achieved by a chemical reaction resulting in the production of carbon dioxide or other gas. The balloon may include at least a first and a second portion or compartment which are separated by be a separation valve or other separation means. A liquid, such as water, can be disposed within the first compartment and at least one reactant disposed in the second compartment which can be liquid though typically is solid. The reactants may include at least two reactants for example, an acid such as citric acid and a base such as sodium bicarbonate, which can have about a 1:2 ratio. Other reactants including other acids, e.g., acetic acid and bases are also contemplated. When the valve or other separation means opens, the reactants mix in the liquid and produce a gas such as carbon dioxide which expands the balloon and advances the tissue penetrating member into the intestinal wall as will be explained more fully herein. In addition to advancing the tissue penetrating members into tissue, the device can also be configured to have the inflated balloon break or otherwise separate apart the capsule into one or more pieces for easier passage through the intestinal tract.

The separation valve can be configured to open in a number of ways and responsive to a number of conditions. For example, the separation valve may be configured to open by having one or more portions degrade in response to the higher pH or other conditions found within the small intestine so that upon degradation, the valve opens. Degradation of the valve allows for mixing of the contents of the first and second compartments and, thus, expansion of the balloon. The separation valve can be positioned on the outside of the capsule or within the capsule interior where it is exposed to intestinal fluids which enter through the at least one aperture or other opening in the capsule. At least a portion of the capsule surface, including the portion containing the at least one aperture, may be coated with a protective layer, such as an enteric coating which also degrades in response to pH or other conditions within the small intestine. Such coatings provide a protective seal over the at least one aperture so that digestive fluids do not enter the capsule interior and start to degrade the separation valve until the capsule has reached the small intestine. As an alternative or additional embodiment, the valve may also be configured to open in response to compressive forces applied by a peristaltic contraction within the small intestine, after a certain period of time has elapsed, or in response to external activation by the patient.

In an alternative embodiment, the balloon can include a liquid such as water or saline in a first compartment and in the second compartment, electrodes connected to a battery. When the capsule reaches the small intestine, the degradation of the valve allows for water or saline to flow into the second compartment. The battery can be activated to apply a voltage across the electrodes and initiate hydrolysis, generating hydrogen and oxygen gases at the electrodes which expands the balloon.

In an additional embodiment, the balloon may include a mixture of sodium azide, SiO2, and KNO3. A sensor, which when exposed to pH with the small intestine, can generate an electrical pulse which ignites the sodium azide, causing it to decompose into nitrogen gas and sodium metal. The sodium metal can then be deactivated by reaction with SiO2 and KNO3 while the nitrogen gas expands the balloon.

Alternatively, the balloon can be an osmotic membrane encapsulating a salt, such as sodium chloride, or other osmotic agent. An enteric coating can be present over the osmotic membrane. When the capsule reaches the intestine, the enteric coating over the osmotic membrane can dissolve, allowing fluid ingress into the balloon and thus expanding the balloon.

In other embodiments, the expandable member can be a superabsorbent hydrogel such as polyacrylate gels used in disposable diapers. An enteric coating can be present on the superabsorbent hydrogel. When the capsule reaches the small intestine, fluid ingress into the capsule causes the enteric coating to degrade and the superabsorbent hydrogel to expand.

In other embodiments, the expandable member can be a pH triggered expanding polymer such as poly(acrylate)-based copolymers, poly(acrylamide) polymers, or poly(m-ethylacrylic acid). The polymer can expand at a pH levels found in the intestines but not in the stomach.

In some embodiments, the expandable member is a shape memory material such as nitinol (nickel titanium) that is tethered in compressed form in place by a degradable release. When the capsule reaches a target site in the GI tract such as the small intestine, fluid ingress into the capsule can result in the degradation of the release, allowing the shape memory material to spring into its expanded shape.

In certain embodiments, the expandable member is an artificial muscle, e.g., an electroactive polymer, that can expand in the presence of an external stimulus such as voltage, current, pressure or temperature. Electroactive polymers such piezoelectric polymers, dielectric actuators (DEAs), electrostrictive graft elastomers, liquid crystal elastomers (LE) and ferroelectric polymers can be activated to expand in the capsule by an electronically controlled system once the capsule reaches a target area of the GI tract.

In addition to the release valve, the balloon or other expandable member can also include a deflation valve which serves to deflate the expandable member after inflation. The deflation valve can comprise biodegradable materials which are configured to degrade upon exposure to the fluids in the small intestine and/or liquid in one of the compartments of the balloon so as to create an opening or channel for escape of gas within balloon. One or more puncture elements can also be attached to the inside surface of the capsule wall such that when the balloon fully deflates it contacts and is punctured by the puncture element.

Additionally, selectable portions of the capsule can be fabricated from such biodegradable materials so as to allow the entire device to controllably degrade into smaller pieces, facilitating passage and excretion through the GI tract. In some embodiments, the capsule can include seams of biodegradable material which controllably degrade to produce capsule pieces of a selectable size and shape to facilitate passage through the GI tract. The seams can be pre-stressed, perforated or otherwise treated to accelerate degradation.

The tissue penetrating member(s) may comprise a hollow or solid needle or other like structure, with or without a lumen or other compartment and a tissue penetrating end for penetrating a selectable depth into the intestinal wall. The lumen may be pre-loaded or filled with functionalized particles. At least one guide tube, within which the penetrating member(s) may be disposed, may also be provided. In some examples, the capsule includes multiple tissue penetrating members and they may have a number of arrangements. Each of the penetrating members can carry the same or different types of particles (i.e., particles functionalized with a different receptor). The former provides for larger amounts of delivery of a particular type of particle, the later allows delivery of particles targeted for two or more different blood analytes at about the same time. The multiple tissue penetrating members may be symmetrically distributed or placed in other patterns around the perimeter of the capsule or on the surface of the expandable member so as to anchor the capsule into the intestinal wall during delivery of the particles.

The tissue penetrating member can be fabricated from a biodegradable polymer such as PGLA so as to degrade within the small intestine and provide a fail-safe mechanism for detaching from the intestinal wall should it become retained there. In such embodiments, the penetrating member may be fabricated from a mixture of particles and biodegradable polymer, so as to deliver the particles upon degradation of the biodegradable polymer by the interstitial fluids within the wall tissue. The penetrating member can also include one or more tissue retaining features such as a barb or hook to retain the penetrating member within the tissue of the intestinal wall after advancement. The retaining features can be arranged in various patterns to enhance tissue retention such as two or more barbs symmetrically distributed around the member shaft. In further embodiments, the tissue penetrating member may also be fabricated from a drug, therapeutic agent, contrast agent or other substance configured to release the functionalized particles upon its degradation and absorption into the body.

In additional embodiments, the tissue penetrating members can be fabricated as wafers or patches containing multiple solid penetrating members and attached to a flexible polymeric support or backing. In some embodiments, the penetrating members are attached via an adhesive to a support. In other embodiments, the penetrating members can be molded onto the support.

As an additional or alternative embodiment to the use of particle-carrying tissue penetrating members, various embodiments of the device can also include reservoirs of particles disposed in the capsule which are compressible by expansion of the balloon or other expandable member. The reservoirs contain the particles either in a dry form, or suspended in a liquid. In these and related embodiments, the reservoirs are fluidically coupled to advanceable hollow tissue penetrating members such that inflation of the balloon compresses the reservoirs so as to force the particle suspension through tissue penetrating member and into the intestinal wall. Multiple reservoirs are contemplated including two, three, four or more. In particular embodiments, two reservoirs can be coupled to a hollow tissue penetrating member with the reservoirs placed about 180 degrees apart with respect to the lengthwise axis of the penetrating member. Typically, the reservoirs will be fluidically coupled to the hollow penetrating member by means of a connector. Suitable connectors include a t-shaped connector having connectors on either of it lateral ends for the reservoirs a central connector for the hollow tissue penetrating member and a central lumen or channel going to all connectors. Other shapes and connector configurations are also contemplated.

In other example capsules, advancement of the plurality of tissue penetrating members is achieved with an actuator having an expandable member, delivery member and a release. The delivery member is configured to advance the particles from the capsule through the tissue penetrating member lumen and into the intestinal wall. At least a portion of the delivery member may be advanceable within the tissue penetrating member lumen and may be coupled to a portion of the actuator or to the expandable member. The actuator is configured to advance the tissue penetrating member a selectable distance into the intestinal wall as well as to leave the tissue penetrating member within the intestinal wall.

Release of the actuator may be controlled by a release coupled to the actuator. Degradation of the release actuates the actuation mechanism. In many embodiments, the release comprises a material configured to degrade upon exposure to chemical conditions in the small or large intestine such as pH or other particular chemical conditions. Biodegradation of the release from one or more conditions in the small intestine (or other target portion of the GI tract) can be achieved by selection of material properties, such as the amount of cross linking of those materials as well as the thickness and other dimensions. Suitable materials for the release can comprise biodegradable materials such as various enteric materials which are configured to degrade upon exposure to the higher pH or other condition in the small intestine. In particular embodiments, the release can comprise a film or plug that fits over or otherwise blocks the guide tube and retains the tissue penetrating member inside the guide tube and/or capsule. In other embodiments, the release can be shaped to function as a latch which holds the tissue penetrating element in place. In these and related embodiments, the release can be located on the exterior or the interior of the capsule. In the interior embodiments, the capsule and guide tubes are configured to allow for the ingress of intestinal fluids into the capsule interior to allow for the degradation of the release.

In some embodiments, the actuator can be actuated by means of a sensor, such as a pH, chemical or mechanical sensor which detects the presence of the capsule in the small intestine and sends a signal to the actuator (or to an electronic controller coupled to the actuator to actuate the mechanism). Additionally or alternatively, the user may externally activate the actuator to deliver the particles by means of RF, magnetic or other wireless signaling means known in the art. In these and related embodiments, the user can use a handheld device (e.g., a hand held RF device) which not only includes signaling means, but also means for informing the user when the device is in the small intestine or other location in the GI tract. The user may also externally activate the actuator at a selected time period after swallowing the capsule. The time period can be correlated to a typical transit time or range of transit times for food moving through the user's GI tract to a particular location in the tract such as the small intestine.

Another aspect of the invention provides methods for the delivery of particles into the walls of the GI tract using embodiments of the swallowable particle delivery devices. The types and amounts of the particular particles delivered can be titrated for the patient's weight, age or other parameters and for the type of blood analytes for which analysis is desired. In various method embodiments, embodiments of the swallowable particle delivery device can be used to deliver a plurality of functionalized particles for the detection and analysis of one or more blood analytes. In use, such embodiments allow a patient to forgo the necessity of having to take multiple separate doses of particles. Also, they can facilitate a regimen of two or more types of particles that are delivered and absorbed into the small intestine and thus, the blood stream at about the same time. Due to differences in their size, shape, materials and functionalized receptors, different types of particles can be absorbed through the intestinal wall at different rates. Embodiments of the invention address this issue by injecting the particles at about the same time. Further, the various embodiments of the swallowable delivery device provide a means for delivering particles to the bloodstream via the GI tract that might otherwise require injection due to chemical breakdown in the stomach.

It should be understood that the above embodiments, and other embodiments described herein, are provided for explanatory purposes, and are not intended to be limiting.

Further, the term "medical condition" as used herein should be understood broadly to include any disease, illness, disorder, injury, condition or impairment—e.g., physiologic, psychological, cardiac, vascular, orthopedic, visual, speech, or hearing—or any situation requiring medical attention.

II. Illustrative Functionalized Particles

Health-related information of a patient may be obtained by detecting the binding of a clinically-relevant analyte to functionalized particles, for example, microparticles or nanoparticles, introduced into the body. The particles can be functionalized by covalently or otherwise attaching or associating a bioreceptor designed to selectively bind or otherwise recognize a particular clinically-relevant analyte. For example, particles may be functionalized with a variety of bioreceptors, including antibodies, nucleic acids (DNA, siRNA), low molecular weight ligands (folic acid, thiamine, dimercaptosuccinic acid), peptides (RGD, LHRD, antigenic peptides, internalization peptides), proteins (BSA, transferrin, antibodies, lectins, cytokines, fibrinogen, thrombin), polysaccharides (hyaluronic acid, chitosan, dextran, oligosaccharides, heparin), polyunsaturated fatty acids (palmitic acid, phospholipids), plasmids. In other examples, the particle itself may have an inherent receptor or affinity for a target analyte. For example, the particle itself may be a virus or phage with an inherent affinity for certain analytes. As used herein, the term "functionalized particles" may refer to any type, shaped or sized particle (i.e., spheres, rods, flakes, nano- or micro-particles, etc.) having an attached, associated or inherent bioreceptor that has an affinity for a particular blood analyte, disposed thereon or in the vicinity thereof.

The clinically-relevant analyte could be any analyte that, when present in or absent from the blood, or present at a particular concentration or range of concentrations, may be indicative of a medical condition or indicative that a medical condition may be imminent. For example, the clinically-relevant analyte could be an enzyme, hormone, protein, or other molecule. In one relevant example, certain protein biomarkers are known to be predictive of an impending arterial plaque rupture. Such protein biomarkers are known to be present in the blood only directly leading up to and at the onset of an arterial plaque rupture. Plaques that rupture cause the formation of blood clots that can block blood flow or break off and travel to another part of the body. In either of these cases, if a clot blocks a blood vessel that feeds the heart, it causes a heart attack. If it blocks a blood vessel that feeds the brain, it causes a stroke. If blood supply to the arms or legs is reduced or blocked, it can cause difficulty walking and eventually gangrene. The presence of these protein biomarkers in the vasculature may be detected, and the medical condition (i.e., stroke, heart attack) prevented, by providing particles functionalized with a bioreceptor that will selectively bind to this target analyte.

The particles may be made of biodegradable or non-biodegradable materials. For example, the particles may be made of polystyrene. Non-biodegradable particles may be provided with a removal means to prevent harmful buildup in the body. Generally, the particles may be designed to have a long half-life so that they remain in the vasculature or body fluids over several measurement periods. Depending on the lifetime of the particles, however, the user of the wearable device may periodically introduce new batches of functionalized particles into the vasculature or body fluids.

Bioreceptors can be used in diagnostic procedures, or even in therapy to destroy a specific target, such as antitumor therapy or targeted chemotherapy. The particles may be designed to remove from the body or destroy the target analyte such as a circulating tumor cell once bound to the bioreceptor. Additional functional groups may be added to the particles to signal that the particles can be removed from the body through the kidneys, for example, once bound to the target analyte.

Further, the particles may be designed to either releasably or irreversibly bind to the target analyte. For example, if it is desired for the particles to participate in destruction or removal of the target analyte from the body, as described above, the particles may be designed to irreversibly bind to the target analyte. In other examples, the particles may be designed to release the target analyte after measurement has been made, either automatically or in response to an external or internal stimulus.

Those of skill in the art will understand the term "particle" in its broadest sense and that it may take the form of any fabricated material, a molecule, cryptophan, a virus, a phage, etc. Further, a particle may be of any shape, for example, spheres, rods, non-symmetrical shapes, etc. The particles can have a diameter that is less than about 20 micrometers. In some embodiments, the particles have a diameter on the order of about 10 nm to 1 µm. In further embodiments, small particles on the order of 10-100 nm in diameter may be assembled to form a larger "clusters" or "assemblies on the order of 1-10 micrometers. In this arrangement, the assemblies would provide the signal strength of a larger particle, but would be deformable, thereby preventing blockages in smaller vessels and capillaries.

Binding of the functionalized particles to a target analyte may be detected with or without a stimulating signal input. The term "binding" is understood in its broadest sense to include any detectable interaction between the receptor and the target analyte. For example, some particles may be functionalized with compounds or molecules, such as fluorophores or autofluorescent, luminescent or chemiluminescent markers, which generate a responsive signal when the particles bind to the target analyte without the input of a stimulus. In other examples, the functionalized particles may produce a different responsive signal in their bound versus unbound state in response to an external stimulus, such as an electromagnetic, acoustic, optical, or mechanical energy.

In other embodiments, the functionalized particles can be labeled with active transport ligands which can assist in actively transporting the particles across an epithelial layer such as the one present on the small intestinal wall. Representative active transport ligands include FCRn receptors which can assist in actively transporting the functionalized particles across the epithelial barrier via the FCRn receptor-mediated endocytosis mechanism with exocytosis on the basolateral side of the epithelial cells. Other active transport ligands include vitamin B12, integrin receptors as well as saccharides.

Further, the particles may be formed from a paramagnetic or ferromagnetic material or be functionalized with a magnetic moiety. The magnetic properties of the particles can be exploited in magnetic resonance detection schemes to enhance detection sensitivity. In another example, an external magnet may be used to locally collect the particles in an area of subsurface vasculature during a measurement period. Such collection may not only increase the differential velocity between particles and analytes, hence surveying a much larger volume per unit time, but may also enhance the signal for subsequent detection.

III. Example Swallowable Devices

One or more embodiments of the devices described herein can be used for the delivery of functionalized particles to the body for the identification and measurement of blood analytes to assess physiological parameters, which may indicate certain health-related conditions. The bioreceptors associated with or otherwise functionalized with the particles may include molecules, compounds or other substances that may be ill-suited for traditional oral delivery because they are susceptible to digestion, degradation or break-down by the digestive fluids in the stomach and/or the lumen of the small intestine. However, rather than being limited to delivering these sensitive functionalized particles via injection and/or IV infusion, they may be taken orally through use of the device. Embodiments of the delivery device allow functionalized particles to be delivered into the wall of the small intestine (or other targeted delivery site) and subsequently absorbed into the blood stream with minimal or no loss of activity of the functionalized receptor, e.g., in the case of an antibody, minimal or no loss in affinity and/or specificity to a target analyte; in the case of any polypeptide, minimal or no loss in affinity and/or specificity to a target analyte; etc. For receptors that would otherwise be partially degraded or poorly absorbed in the GI tract, the amount or dose of functionalized particles to achieve accurate identification and measurement of the target blood analyte can be less than the amount required should the particles have been delivered by conventional oral delivery (e.g., as a drinkable suspension of particles, or as a swallowable pill that is digested in the stomach and absorbed through the wall of the small intestine). Because the particles are delivered directly into the wall of the small intestine (or other target portion of the gastrointestinal tract, e.g., large intestine, stomach, etc.), embodiments of the device described herein can provide protection to the sensitive functionalized particles, allowing for little or no degradation of the particles or their receptors by acid and other digestive fluids in the stomach.

Further, embodiments of the device provide an advantage of allowing for the delivery of multiple types of functionalized particles in a single dose or capsule. As described above, particles functionalized with different receptors may be used to identify and measure different blood analytes, each type of particles providing information about a different physiological parameter or an indication of a different aspect of the health state of the patient. In use, such embodiments allow a patient to forgo the necessity of having to take separate doses of particles, each specific to a particular target analyte. Also, the delivery device can enable a combination of functionalized particles and another agent, such as a contrast agent, fluorophore, enzyme, reactant, etc., to be delivered and absorbed into the small intestine and thus, the blood stream, at about the same time. Such timing may be important for the additional agent to provide some assistance or benefit to the action of the functionalized particles. Additionally, eliminating the need to take multiple doses of functionalized particles may be beneficial to patient compliance and timing.

Figure 4:
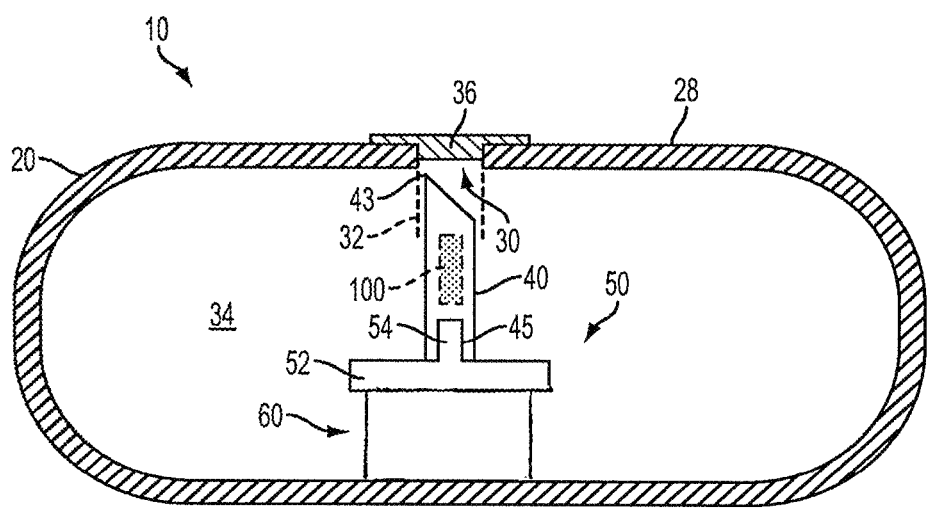
FIG. 4 is a side sectional view of an embodiment of a swallowable delivery device.

Referring now to the Figures, embodiments of a device 10 for the delivery of functionalized particles 100 to the intestinal tract are shown. As shown in FIGS. 1 and 4, in one embodiment, the device 10 may comprise a capsule 20 sized to be swallowed and pass through the intestinal tract, a plurality of tissue penetrating members 40 (although only one penetrating member is shown for illustrative purposes), and actuator 50. Generally, capsule 20 may be provided in many sizes, depending on the target delivery site, the age, height, weight and gender of the patient, and the amount of functionalized particles intended to be delivered with the device 10. Capsule lengths can be in the range of 1 to 5 cm and diameters in the range of 0.25 to 1.5 cm, with other dimensions contemplated. The capsule 20 may be of any shape, including those known in the art, such as pill or tablet shaped.

One or more portions of capsule 20 can be fabricated from various biocompatible polymers known in the art, including various biodegradable polymers which in a preferred embodiment can comprise PGLA (polylactic-co-glycolic acid). Other suitable biodegradable materials include various enteric materials described herein as well as lactide, glycolide, lactic acid, glycolic acid, para-dioxanone, caprolactone, trimethylene carbonate, caprolactone, blends and copolymers thereof. Use of biodegradable materials for capsule 20, including biodegradable enteric materials allows the capsule to degrade in whole or part to facilitate passage through the GI system after delivery of the functionalized particles.

In some embodiments, the capsule 20 can include one or more seams 22, configured to segment the capsule 20 into two or more pieces. In some examples, the seams 22 may be pre-stressed, scored, or perforated regions configured to cause the capsule material to physically break, tear, rip or otherwise fail in those regions. In other examples, the seams 22 may be made of biodegradable material and can also include pores or gaps for ingress of fluids into the seam to accelerate biodegradation. The seams 22 may also be made from a material designed to biodegrade faster than the material chosen for the remainder of the capsule 20. In still other embodiments, seams 22 can be constructed of materials and/or have a structure which is readily degraded by absorption of ultrasound energy, e.g. high frequency ultrasound (HIFU), allowing the capsule to be degraded into smaller pieces using externally or endoscopically (or other minimally invasive method) administered ultrasound. Seams 22 can be attached to capsule body 20 using various joining methods known in the polymer arts such as molding, hot melt junctions, etc. Capsule 20 can also be fabricated from two or more separate joinable pieces that can be adhered together or, alternatively, joined by a mechanical fit such as a snap or press fit.

The capsule 20 can also include a marker 26 designed to assist in locating the capsule as it travels through the GI tract. Marker 26 may be fabricated from certain radio-opaque or echogenic materials for location of the device using fluoroscopy, ultrasound or other medical imaging modality. Use of a marker 26 may also allow for the determination of transit times of the device 10 through the GI tract.

A plurality of tissue penetrating members 40 are provided, as shown generally in FIG. 4, in the interior 34 of the capsule. In some embodiments, tissue penetrating members 40 can be positioned within or aligned with guides 32 which may serve to guide members 40 through the one or more apertures 30 in the capsule wall 28 and into tissue, such as the wall of the small intestine or other portion of the GI tract.

A cap 36 may be provided to cover aperture 30 to protect the capsule interior 34 and its contents while the capsule 20 travels through the stomach and GI tract on its way to the target delivery site. As will be described further below, cap 36 fits over or otherwise blocks guide tubes 30 and may act to retain the tissue penetrating member 40 inside the guide tube 30. Cap 36 may be fabricated from a biodegradable material such as an enteric coating material, chosen to degrade once the capsule reaches a certain region of the GI tract.

Turning to FIGS. 2A-2E, tissue penetrating members 40 may comprise a lumen 41, having an opening 42, and a tissue penetrating end 43, which may be pointed so as to readily penetrate tissue of the intestinal wall. In further examples, rather than having a lumen through which functionalized particles 100 may be delivered, tissue penetrating member 40 may instead have an internal compartment 46 in which a plurality of functionalized particles, or a preparation containing them, may be housed for delivery as shown in FIG. 2D. The tissue penetrating member 40 can be solid with functionalized particles 100 dispersed throughout as shown in FIG. 2E. Tissue penetrating member may, in such examples, be fabricated from a biodegradable material so as to release functionalized particles 100 from compartment 46 upon degrading in the intestinal wall.

Tissue penetrating member may be designed to enhance the retention of tissue penetrating member 40 in the intestinal wall. In some examples, one or more retaining elements 44, such as a barb or hook, may be provided along the length of tissue penetrating member 40 to retain the penetrating member within the intestinal wall after deployment. Retaining elements 43 can be arranged in various patterns, longitudinally and/or radially, to enhance tissue retention. For example, as shown in FIG. 2C, two or more barbs may be distributed around and along member 40. In some embodiments, such as is shown in FIG. 2B, tissue penetrating member 40 may have a generally tapered shape. Peristaltic contractions from the intestinal tract acting on the tapered body may act to force or squeeze the member 40 farther into the intestinal wall.

Tissue penetrating member 40 can be fabricated from any biocompatible materials known in the art having the desired structural properties. In some examples, tissue penetrating members may be fabricated from one or more biodegradable polymers so as to degrade after delivery of functionalized particles 100. Such biodegradation can, as described above, act to release particles internally housed in the member 40, and to allow member 40 to be broken down and cleared from the body. Additionally, tissue penetrating members 40 may be fabricated from one or more other agents, such as medicinal, therapeutic or imaging contrast agents, which may provide some therapeutic or imaging enhancement to facilitate use of the functionalized particles 100. In some cases, the functionalized particles may be carried by the tissue penetrating member 40 by mixing them in with a biodegradable material, such as PGLA, cellulose or maltose, to form tissue penetrating member 40. Once delivered to the intestinal wall, the penetrating member 40 is degraded by the interstitial fluids within the tissue, thereby releasing the particles making up, in part, the member itself. Tissue penetrating member 40 can be fabricated using one or more polymer and pharmaceutical fabrication techniques known in the art, with particular attention paid to preventing any substantial thermal or chemical degradation of the functionalized particles.

The functionalized particles 100 may be delivered to the intestinal wall in a variety of ways. In general, the plurality of tissue penetrating members 40 will be advanced into the intestinal wall via an actuator 50 and the functionalized particles will be delivered to the tissue via the plurality of tissue penetrating members 40. The functionalized particles 100 themselves may be delivered alone or in combination with another substance. For example, functionalized particles 100 may be combined with a pharmaceutically acceptable liquid to form a suspension preparation. Functionalized particles 100 may also be combined with any number of pharmaceutically acceptable gels, solids or powders to form solid or semi-solid preparations that may be designed to retain a particular shape, such as a pellet. Further, as described above, the preparation containing functionalized particles 100 may also include any number of other pharmaceutically acceptable excipients or substances, such as drugs, or therapeutic or imaging agents.

As shown in FIGS. 2A and 2B, the functionalized particles may be pre-packed within the lumen 41 of tissue penetrating members 40. In other examples, as shown in FIGS. 2C, 2D and 2E, delivery of the functionalized particles 100 can be achieved through degradation of the tissue penetrating member itself. Tissue penetrating member can include a passage 47 into which functionalized particles may be introduced and housed for delivery, as shown in FIG. 2C. Alternatively, the tissue penetrating member 40 can include an integral internal compartment 46 containing functionalized particles 100 into which functionalized particles 100 are introduced during manufacture of member 40. As described above, the functionalized particles 100 may also be mixed with a biodegradable polymer and used to fabricate the body of the tissue penetrating member 40 itself, as shown in FIG. 2E. It is also contemplated that functionalized particles can be contained at another location within an interior 34 of capsule 20.

Figure 3:
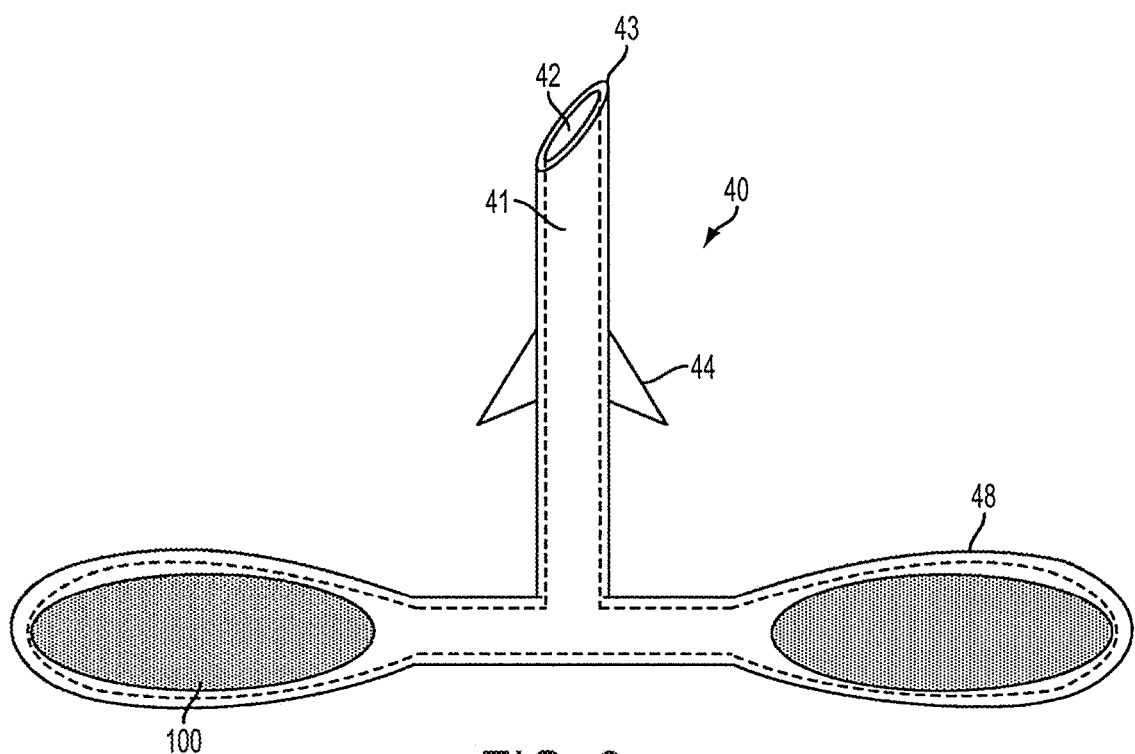
FIG. 3 is a side view of an embodiment of a tissue penetrating member for use in a swallowable delivery device.

Tissue penetrating members 40 may also be fluidically connected to one or more reservoirs 48 containing functionalized particles. In one example shown in FIG. 3, tissue penetrating member 40 is connected to two reservoirs 48. The reservoir 48 may be made of a compressible material, whereby compression thereof acts to force functionalized particles 100 contained therein into the lumen 40 and into the issue via opening 42. The reservoirs 48 can contain the functionalized particles 100, or a preparation containing them, in a dry or suspended form.

The device 10 can be configured for delivery of a single or of multiple types of functionalized particles 100. If multiple tissue penetrating members 40 are provided, each may be used to deliver a different type of functionalized particle. Similarly, different types of particles can be contained within separate compartments or reservoirs 48 within capsule 20.

Device 10 also includes an actuator 50 coupled, either directly or indirectly, to the at least one tissue penetrating member 40. The actuator 50 is configured to advance the functionalized particles 100 from within the capsule into a wall of a lumen of the gastrointestinal tract via the plurality of tissue penetrating members 40. The actuator 50 may include an expandable member 60, which can comprise a variety of expandable devices shaped and sized to fit within capsule 20. In some examples, expandable member comprises an expandable balloon 64. Other suitable expandable members include various shape memory devices, and/or chemically expandable polymer devices having an expanded shape and size corresponding to the interior volume 34 of the capsule 20.

Generally, actuator 50 has at least a first, or retracted, configuration and a second, or deployed, configuration. In the first configuration, actuator 50 is configured to retain the functionalized particles within the capsule. The actuator 50 is configured to transition from the first configuration to the second configuration, thereby advancing the plurality of functionalized particles from the capsule into an intestinal wall. Transitioning from the first to the second configuration may be achieved by expansion of expandable member 60.

Figure 5:
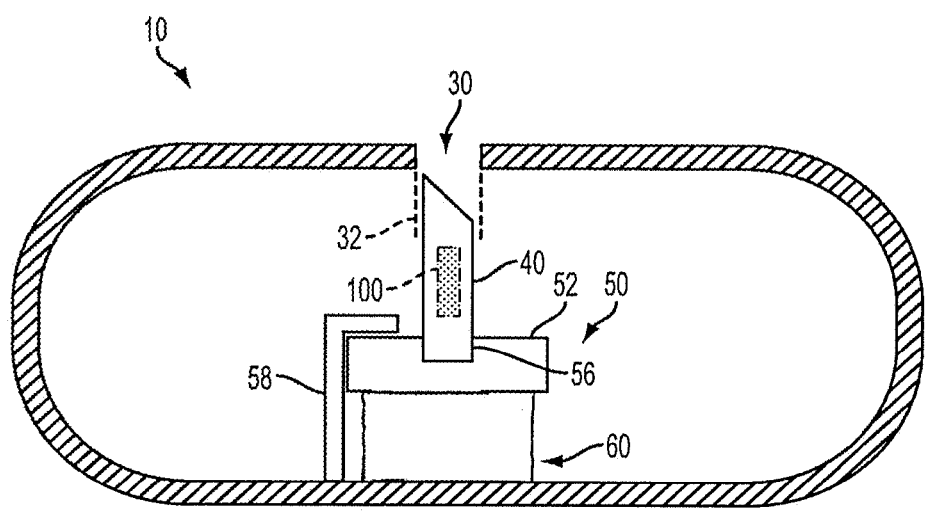
FIG. 5 is a side sectional view of an embodiment of a swallowable delivery device.

Actuator 50 may also include a support 52, on or in which tissue penetrating members 40 may be placed, which may serve to stabilize members 40 and couple them to actuator 50. Support 52 may include a key 54 for mating with a notch 45 on tissue penetrating member 40. Alternatively, support 52 may include an inset 56 for tissue penetrating member 40 to fit therein. Support 52 may be a flat flexible backing such as a polymer substrate or tape which includes an adhesive to releasably attach members 40. A release 58 designed to releasably maintain the actuator in the first configuration may be directly or indirectly coupled to one or more of the actuator 50, expandable member 60 or tissue penetrating member 40. In some embodiments, the release can mechanically block the guide tube and retain the tissue penetrating member inside the guide tube and/or capsule. For example, cap 36 as shown in FIG. 4 may physically act on tissue penetrating member 40 to retain actuator 50 in a compressed state. In other embodiments, the release element can be shaped to function as a latch which holds the tissue penetrating member 40 in place or the expandable member 60 in a contracted state, as shown in FIG. 5.

Actuator 50 may be configured such that expandable member 60 directly or indirectly advances tissue penetrating members 40 through apertures 30 and into the intestinal wall. In the embodiments shown in FIGS. 4 and 5, expansion of expandable member 60 directly advances expandable member 40 out through aperture 30 in the direction of expansion. As will be described further below, actuation of the expandable member can be inhibited by a release until the device 10 reaches the target delivery site.

Release 58 can be configured to degrade in response to other conditions in the small intestine (or other GI location). In particular embodiments, the release 58 can be configured to degrade in response to particular chemical conditions in the fluids in the small intestine such as those which occur after ingestion of a meal (e.g., a meal containing fats, starches or proteins). In this way, the release of functionalized particles 100 can be substantially synchronized or otherwise timed with the digestion of a meal.

Suitable enteric or biodegradable materials for the release include, but are not limited to, the following: cellulose acetate phthalate, cellulose acetate trimellitate, hydroxypropyl methylcellulose phthalate, polyvinyl acetate phthalate, carboxymethylethylcellulose, copolymerized methacrylic acid/methacrylic acid methyl esters as well as other enteric materials known in the art. The selected enteric materials can be copolymerized or otherwise combined with one or more other polymers to obtain a number of other particular material properties in addition to biodegradation. Such properties can include without limitation stiffness, strength, flexibility and hardness.

Additionally or alternatively, release 58 may also be provided as or with a sensor, such as a pH sensor or other chemical sensor which detects the presence of the capsule 20 in the small intestine, thereby triggering release of the actuator 50. Embodiments of a pH sensor can comprise an electrode or a mechanically-based sensor such as a polymer which shrinks or expands upon exposure to a selected pH or other chemical conditions in the small intestine. In one example, the release 58 may comprise a sensor that upon exposure to a selected pH or other condition releases or causes the release of an electrical pulse or electrical current which drives a chemical reaction, thereby triggering release of the actuator 50. In other examples, release 58 may comprise an expandable/contractible sensor, configured to release actuator 50 using the mechanical motion from the expansion or contraction of the sensor.

In some examples, after delivery to the intestinal wall, tissue penetrating member(s) 40 may be detached from the actuator 50 and retained in the tissue. For example, tissue penetrating member 40 may be configured to be detachably coupled (directly or indirectly) to the expandable member 60, such as a balloon 64 (as described below), so that after advancement of the tissue penetrating member 40 into the intestinal wall, the penetrating member detaches from the expandable member 60. Detachability can be implemented by a variety of means including: i) the configuration and strength of the joint between penetrating member 40 and actuator 50 or other intermediary component(s), such as support 52; 2) the configuration and placement of tissue retaining features 44 on penetrating member 40; and iii) the depth of penetration of tissue penetrating member 40 into the intestinal wall. Using one or more of these means, penetrating member 40 be configured to detach as a result of retraction of the expandable member 60 (where the retaining features 44 hold the penetrating member in tissue as expandable member detracts or otherwise pulls back away from the intestinal wall) and/or the forces exerted on capsule 20 by a peristaltic contraction of the small intestine.

After delivery, device 10 and its components degrade, at least in part, then pass through the intestinal tract including the large intestine and are ultimately excreted. Where the capsule 20 is tearable and/or has biodegradable seams 22 or other biodegradable portions, the capsule may break down into smaller pieces in the intestinal tract to facilitate passage through and excretion from the body. Alternatively, the capsule can be bio-degradable and completely dissolve in the intestinal tract. In particular embodiments, tissue penetrating members 40 can be biodegradable. Thus, should the member get stuck in the intestinal wall, it may biodegrade releasing the capsule 20.

Figure 6:
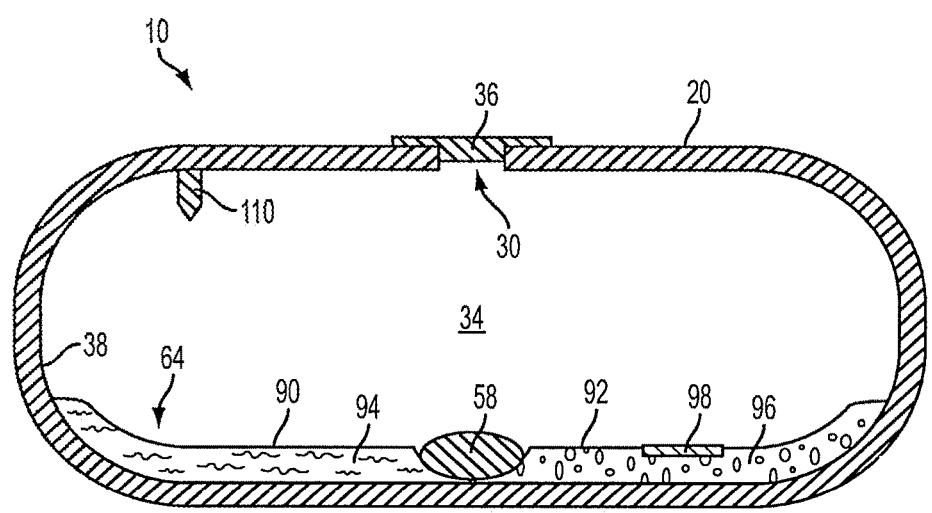
FIG. 6 is a side sectional view of an embodiment of a tissue penetrating member for use in a swallowable delivery device.

Turning now to FIG. 6, in other embodiments of device 10, expandable member 60 of actuator 50 may be provided as a balloon 64. Balloon 64 can be attached to an interior surface 38 of the capsule 20 in a non-expanded state. Means of attachment can include the use of various adhesive known in the medical device arts. The balloon can be packed inside capsule 20 in a furled or other compact configuration to conserve space within the interior portion of the capsule.

Balloon 64 can be fabricated from various polymers, including types of polyethylene (PE) which may correspond to low density PE (LDPE), linear low density PE (LLDPE), medium density PE (MDPE) and high density PE (HDPE) and other forms of polyethylene known in the art. The material may be cross-linked using polymer irradiation methods known in the art to control the inflated diameter and shape of the balloon by decreasing the compliance of the balloon material. Other suitable polymers can include PET (polyethylene terephalate), silicone and polyurethane. Balloon 64 may also include various radio-opaque materials known in the art such as barium sulfate to allow a physician to ascertain the position and physical state of the balloon (e.g., un-inflated, inflated or punctured).

The balloon 64 may be fabricated using various balloon blowing methods known in art (e.g., mold blowing) to have a shape and size which corresponds approximately to the interior volume 34 of capsule 20. In some embodiments, the inflated size of the balloon can be configured to provide improved contact between the capsule/balloon surface and the intestinal wall so as to effectively deploy tissue penetrating members 40 and deliver functionalized particles 100. For example, the balloon can be sized, such that when inflated, it smooths the folds of the small intestine. In some embodiments, the inflated size of balloon 64 can be slightly larger than capsule 20 so as to cause the capsule to come apart or otherwise fail from the force of inflation. The walls of balloon 64 may have a thickness in the range of 0.1 to 0.002 mm. In some embodiments, the walls of the balloon 64 have a thickness in the range of 0.02 to 0.002 mm. In further embodiments, the walls of the balloons 64 may be provided with wall thicknesses of 0.013, 0.01, 0.007, 0.005, or 0.003 mm.

Figure 9A:
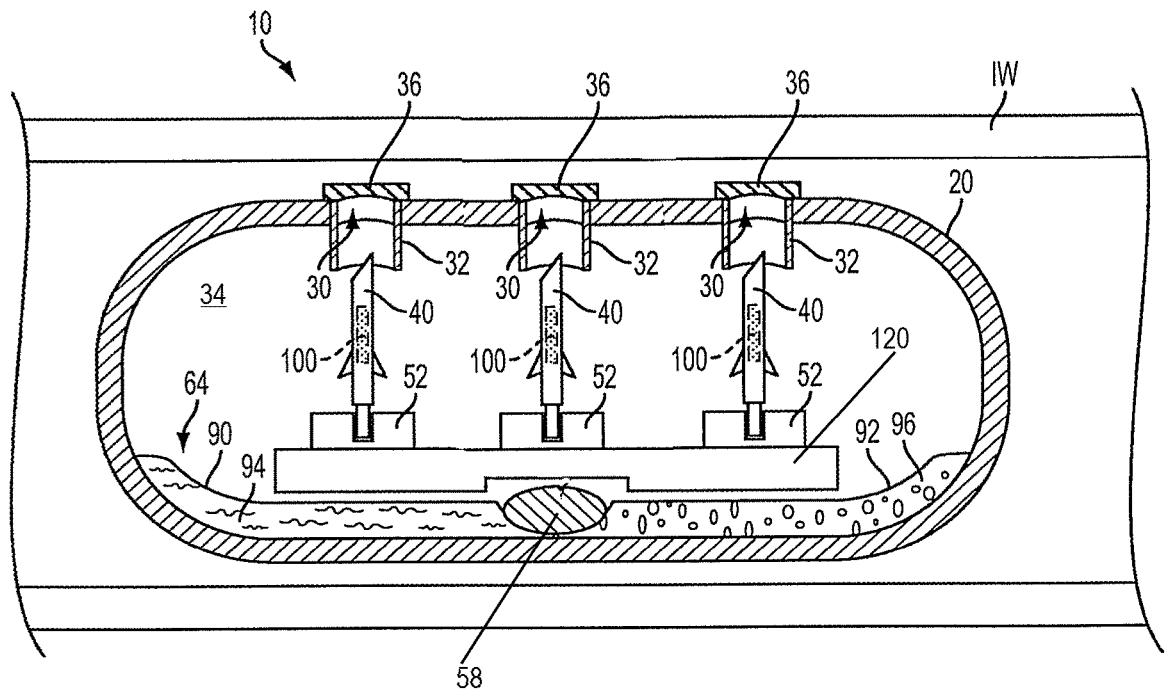
FIGS. 9A-9C are side sectional views of an embodiment of a swallowable delivery device, shown in a lumen of the intestinal tract.
Figure 9B:
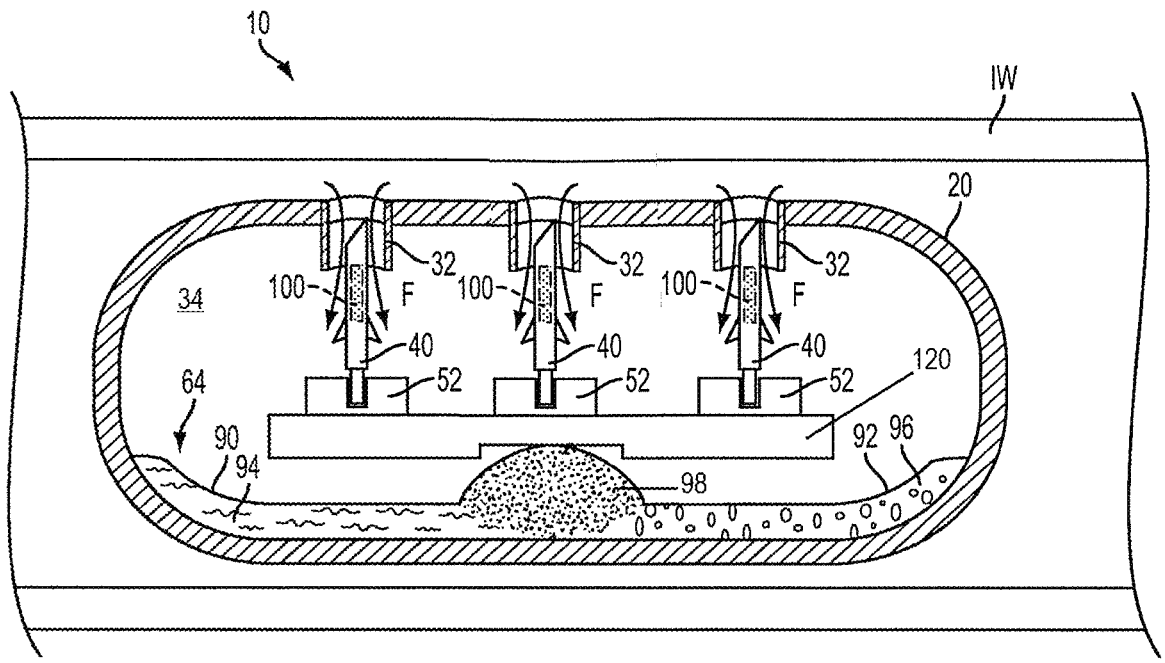
Figure 9C:
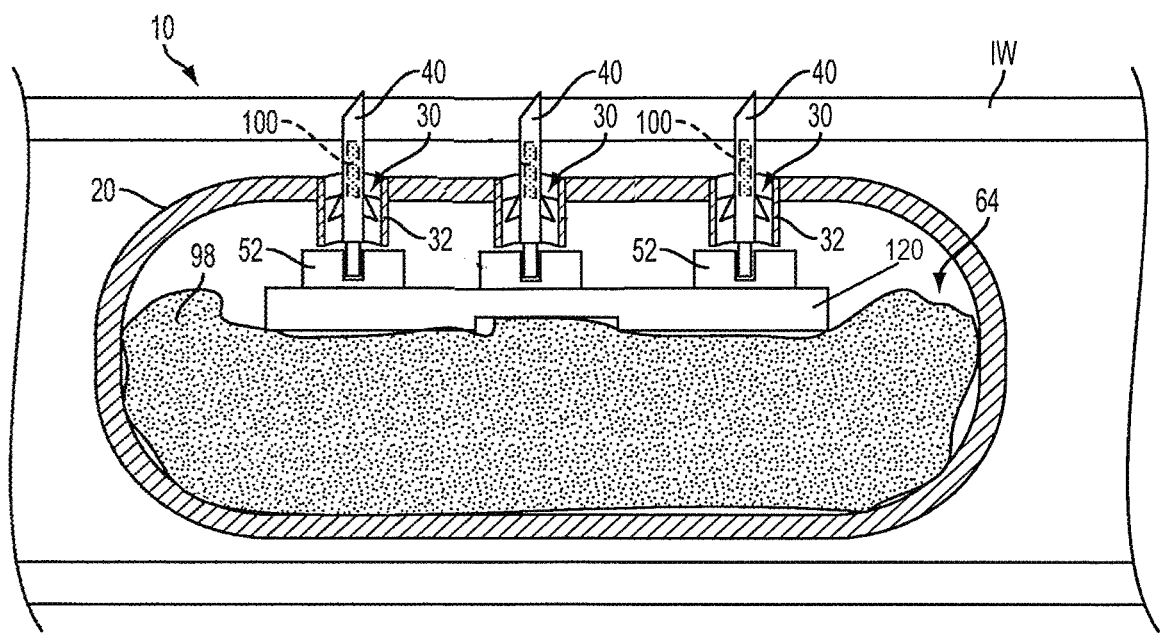

Balloon 64 may include at least first 90 and second 92 compartments which are separated by a release 58, which separates the contents of each compartment. First and second compartments 90, 92 each house a substance that, when mixed, will react to generate a gas that will expand balloon 64. A liquid 94, in some cases water, can be disposed within first compartment 90 and one or more reactants 96 disposed in second compartment 92. Reactants 96 may be solids or liquids. When release 58 is triggered (e.g., from degradation caused by fluids within the small intestine), liquid 94 enters second compartment 92 (or vice versa or both), the reactant(s) 96 mix with the liquid and produce a gas 98, such as carbon dioxide, which expands balloon 64 as is shown in the embodiments of FIGS. 9A-9C. Expansion of balloon 64 is configured to advance functionalized particles 100 into the intestinal wall IW, via the plurality of tissue penetrating members 40.

Reactants 96 may include an acid such as citric acid and a base such as sodium bicarbonate. Additional numbers of reactants are also contemplated. For embodiments using citric acid and sodium bicarbonate, the ratios between the two reactants (citric acid to sodium bicarbonate) can be in the range of 1:1 to 1:4, with a specific ratio of 1:2. Solid reactants, such as sodium bicarbonate, can be pre-dried (e.g., by vacuum drying) before being placed within balloon 64. Other reactants 96, including acetic acid are also contemplated. The amounts and selected combinations of particular reactants 96 can be chosen to produce particular pressures using known stoichiometric equations for the particular chemical reactions as well as the inflated volume of the balloon and the ideal gas law (e.g., $PV=nRT$).

Balloon 64 or other expandable member 60 may also include one or more deflation valves 98 which serve to deflate balloon 64 after inflation, as shown in FIG. 6. Deflation valve 98 can be fabricated from biodegradable materials which are configured to degrade upon exposure to the fluids in the small intestine and/or liquid in one of the compartments of the balloon so as to create an opening or channel for escape of gas within balloon. Multiple deflation valves 98 can be placed at various locations within balloon wall to provide an even higher degree of reliability in deflation. In general, deflation valve 98 may be fabricated from a degradable material designed to degrade more slowly than the release 58, allowing time for balloon 64 to fully inflate and deliver functionalized particles 100 to the intestinal wall before degrading and deflating the balloon. Additionally, as further backup for insured deflation of balloon 64, one or more puncture elements 110 can be attached to the inside surface 38 of the capsule wall such that when the balloon fully inflates, it contacts and is punctured by the puncture element. Other means for balloon deflation are also contemplated.

Figure 7:
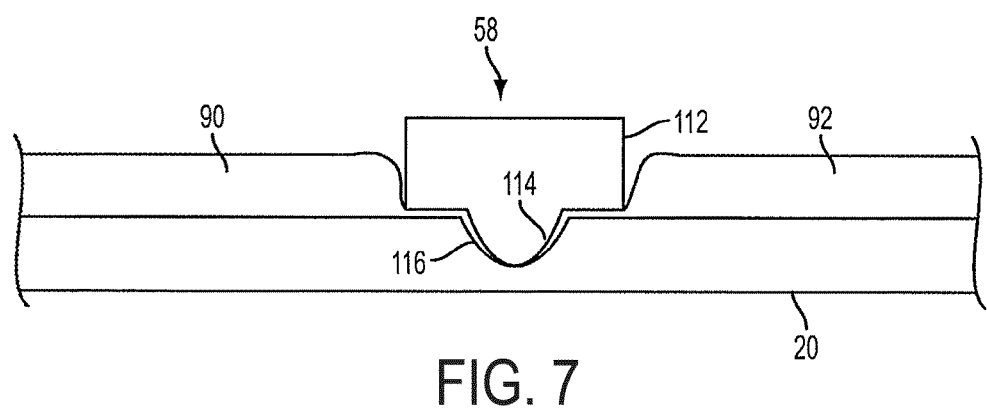
FIG. 7 is an embodiment of a release for use in a swallowable delivery device.
Figure 8:
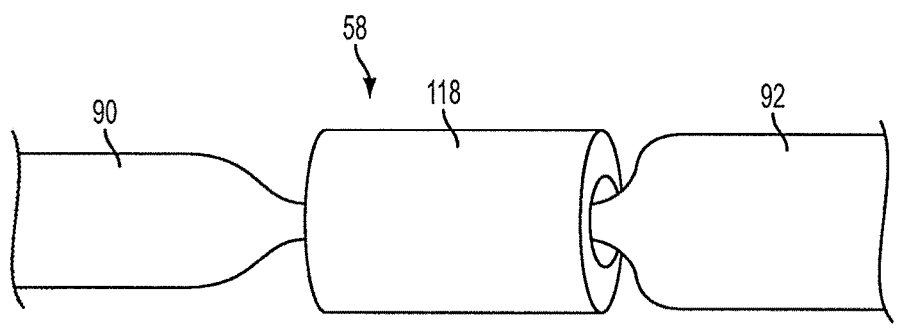
FIG. 8 is an embodiment of a release for use in a swallowable delivery device.

Release 58 may be provided in a number of structures and configurations, including, for example, a pinch valve 112 (FIG. 7) or collar 118 (FIG. 8). Still other structures are considered. In one embodiment, shown in FIG. 7, pinch valve 112 can include one or more protrusions 114 shaped to pinch balloon 64 into a depression 116 on the internal surface 38 of capsule 20. Multiple protrusions 114 may be used to create multiple seal points. According to another embodiment, shown in FIG. 8, the release 58 can comprise a collar 118 for constricting balloon 64 to maintain separation between the first and second compartments 90, 92.

Release 58, such as pinch valve 112 or collar 118, can be configured to open in a number of ways and responsive to a number of conditions within the GI tract. In some embodiments, release 58 will be configured to open by having one or more portions degrade in response to the higher pH or other conditions found within the small intestine. Accordingly, release 58 may be made from biodegradable material, thereby acting to seal first and second compartments 90, 92 and releasing them upon degradation. Release 58 may also be configured to open in response to compressive forces applied by a peristaltic contraction within the small intestine. In still another approach, release 58 may be a time-release valve configured to open after a certain period of time after a trigger event, e.g., an activation step initiated by the patient. In a further embodiment, release may be provided as or with an expandable/contractible pH sensor, configured to expand or contract so as to open a channel between balloon compartments 90 and 92, in response to sensing a particular pH, particularly upon exposure to the pH conditions in the small intestine (e.g., a pH above 6.0, 6.5, 7.0, 7.1, 7.2, etc.).

Further, in some embodiments, at least a portion of the capsule exterior surface, including the portion containing the at least one aperture 30, may be covered with a protective layer or coating, such as an enteric coating which also degrades in response to pH or other conditions within the small intestine. At the very least, the coating may cover aperture 30, in the form of cap 36 for example, so that digestive fluids do not enter the capsule interior 34 and degrade the release 58 until the capsule has reached the small intestine.

Tissue penetrating member 40 can be directly or indirectly coupled to balloon 64. In some embodiments, tissue penetrating member 40 may be positioned in a support 52, to stabilize the member 40 and hold it in the correct position. In further embodiments, tissue penetrating member 40 may be coupled to a platform 120. Platform 120 may comprise a rigid structure attached to the balloon surface on one side and attached to a support 52 on the other, which releasably engages the penetrating member 40. Support 52 may be an independent component, as shown in FIG. 9A, or may be formed integrally with platform 120. Both support 52 and platform 120 may be constructed from biodegradable materials such as PGLA, which can be cross linked and/or copolymerized to have increased rigidity to support the advancement of penetrating members 40 into tissue. Tissue penetrating members 40 can also be directly coupled to platform 120 without necessarily using a support 52, for example by using a protrusions, indentations, or adhesives (not shown). Further, tissue penetrating members 40 may be directly coupled to the balloon 64 e.g., by an adhesive where the adhesive force is less than the necessary to pull penetrating member out of tissue once it is deployed into the intestinal wall. In these and related embodiments, the tissue penetrating members 40 may also be configured to rupture the balloon wall when they detach from the balloon and thus provide a means for balloon deflation.

Support 52 can be configured such that tissue penetrating member 40 will detach therefrom in response to the force of balloon deflation, the force applied to capsule 20 by peristaltic contraction, and/or dissolution of the adhesive attaching the member 40 to support 52. In some embodiments, platform 120 can have a larger horizontal surface area than the surface area of penetrating member 40 so as to function as a force concentration element. In use, platform 120 may function to increase the force per unit area applied to the penetrating member from expansion of balloon 64 or other expandable member. Other structures for loading tissue penetrating members 40 and coupling them to the expandable member 60 are contemplated.

The embodiments of FIGS. 9A-9C illustrate a sequence of degradation of the caps 36, ingress of intestinal or other fluid F into the capsule interior 34 and subsequent degradation of the release 58. In use, embodiments of device 10 employing a degradable cap 36 to cover the aperture 30 and a degradable release 58 provide a primary and secondary seal for assuring that balloon 64 does not prematurely expand and deploy its tissue penetrating members 40 until capsule 20 has reached the small intestine. Upon ingress of intestinal fluid F into the interior 34 of capsule 20, release 58 degrades, allowing liquid 94 disposed within first compartment 90 to mix with the one or more reactants 96 disposed in the second compartment 92 to form a gas 98 (FIG. 9B). As gas 98 is generated, balloon 64 expands filling the interior 34 of capsule 20 thereby forcing platform 120, and coupled tissue penetrating members 40 through guides 32 and out apertures 30. Expansion of balloon 64 forces tissue penetrating members 40 into the intestinal wall IW thereby delivering functionalized particles 100.

Figure 10A:
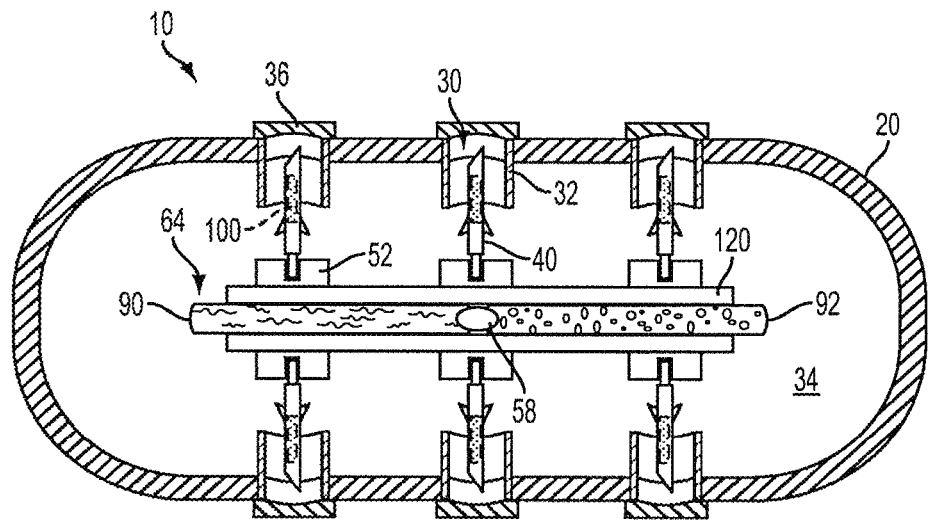
FIG. 10A is a front sectional view of an embodiment of a swallowable delivery device.

Tissue penetrating members 40 can be placed and distributed in a number of locations and patterns on the balloon surface. For example, as shown in FIG. 10A, platforms 120 can be placed on either side of balloon 64 to allow for bilateral deployment of multiple tissue penetrating members 40 into intestinal wall IW. In addition to delivering more functionalized particles 100 at once, bilateral deployment serves to anchor capsule 20 on both sides of the intestinal wall IW during deployment of penetrating members 40, thus reducing the likelihood of the capsule from being dislodged during deployment (e.g., due to peristaltic contraction).

Figure 10B:
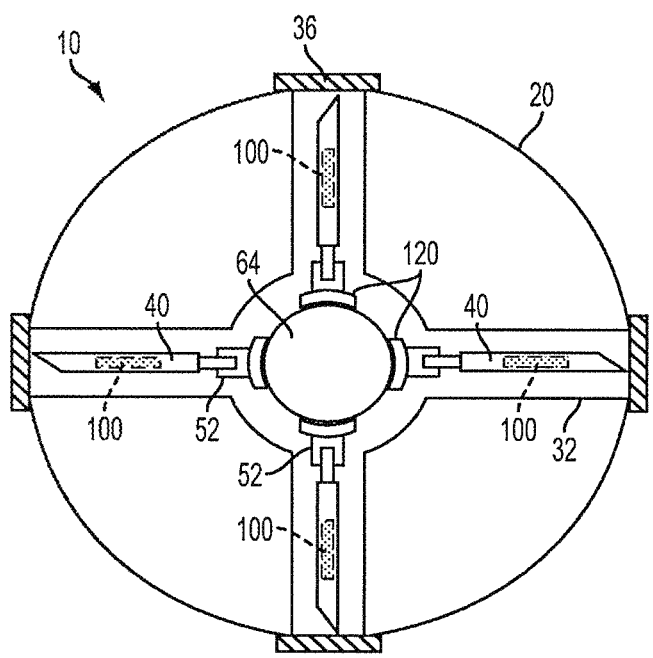
FIG. 10B is a side sectional view of an embodiment of a swallowable delivery device.

In an alternative embodiment, multiple tissue penetrating members 40 on support 52 may also be positioned radially around the expansion member 64, as shown in FIG. 10B, and along its length. Use of such a distributed delivery of functionalized particles 100 into the intestinal wall can function to provide maximum surface area for the radially expanding penetrating members and can also provide for faster absorption of the functionalized particles into the blood stream due to a more even and greater distribution of the functionalized particles within the intestinal wall.

Figure 10C:
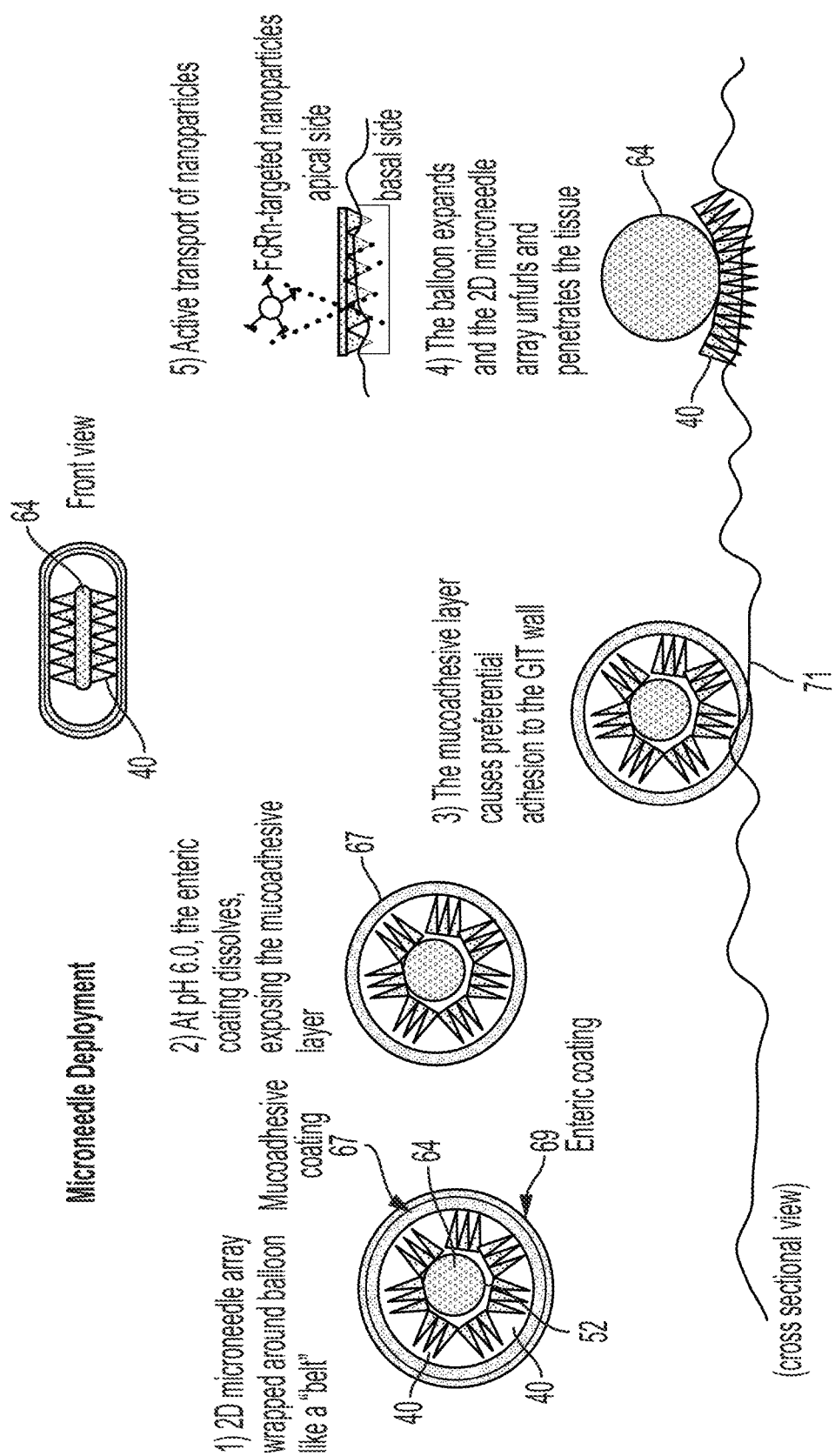
FIG. 10C is a view of an embodiment of a swallowable delivery device, shown in a lumen of the intestinal tract.

In an embodiment, as shown in FIG. 10C, a capsule is provided with includes a mucoadhesive layer 67 and enteric coating 69. Multiple tissue penetrating members 40 on support 52 may be positioned radially around expansion member 64 like a belt. See step (1) of FIG. 10C. At a certain pH, e.g., pH 6.0, the enteric coating 69 dissolves, exposing the mucoadhesive layer 67. See step (2) of FIG. 10C. The exposed mucoadhesive layer 67 causes the capsule to preferentially adhere to the wall 71 of the GI tract. See step (3) of FIG. 10C. The balloon 64 expands, resulting in the array of microneedles 40 to unfurl and penetrate the apical side of the wall 71. See steps (4) and (5) of FIG. 10C. The functionalized particles, e.g, FcRn receptor labeled nanoparticles are then actively transported across the epithelial barrier via FCRn receptor-mediated endocytosis with exocytosis on the basal side of the epithelium.

Figure 11A:
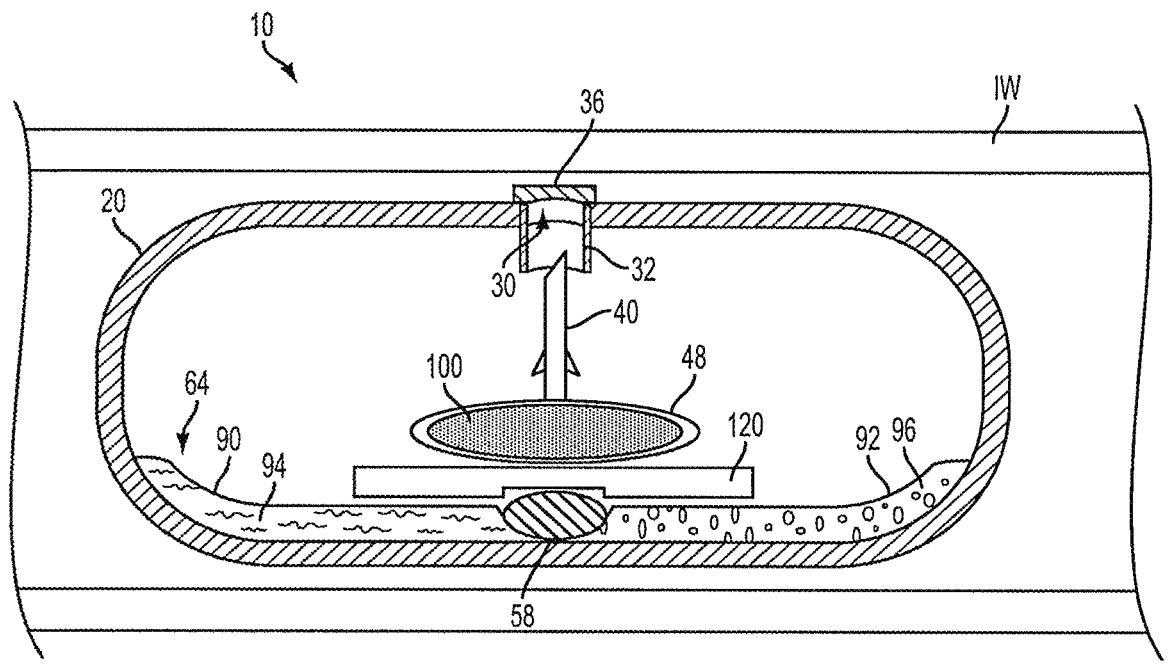
FIGS. 11A-11B are side sectional views of an embodiment of a swallowable delivery device, shown in a lumen of the intestinal tract.
Figure 11B:
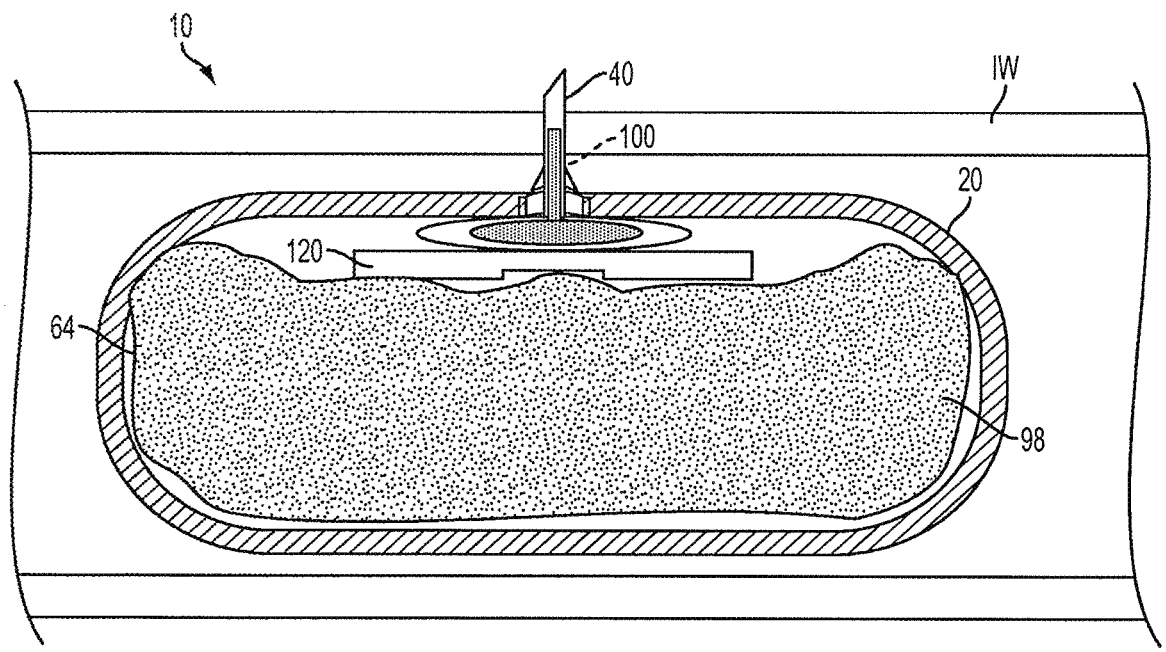

Turning to FIGS. 11A and 11B, tissue penetrating members 40 may also be coupled to one or more reservoirs 48 containing functionalized particles 100. The reservoir 48 may be fluidically coupled to tissue penetrating member 40 such that inflation of balloon 64, or expansion of some other expandable member 60, compresses the reservoirs 48 so as to force the functionalized particles, or a preparation thereof, through the lumen of tissue penetrating member 40 and into the intestinal wall IW, as shown in FIG. 11B.

Further, as an alternative or supplement to internally activated delivery, in some embodiments, the user may externally send a signal to a release 58 or directly to actuator 50 to activate the actuator 50 to deliver functionalized particles 100. This may be achieved by means of RF, magnetic or other wireless signaling means known in the art, such as by use of a controllable valve for example, a radio frequency (RF) controlled miniature solenoid valve or other electro-mechanical control valve (not shown). In other embodiments, release 58 may comprise a controllable isolation valve provided as a miniature magnetically controlled valve such as a magnetically controlled miniature reed switch (not shown). Such electromechanical or magnetic-based valves can be fabricated using MEMS and other micro-manufacturing methods. In these and related embodiments, the user can use an external reader, such as a handheld communication device, mobile device, handheld computer, or other computing device to send and receive signals from device 10.

In such embodiments, swallowable device may also include a transmitter 29 such as an RF transceiver chip or other like communication device/circuitry. External reader may include a signaling means and also a means for informing the user when device 10 is in the small intestine or other location in the GI tract, such as a user interface or display. The external reader can also be configured to alert the user when actuator 50 has been activated and the selected functionalized particles 100 delivered. Such confirmation may allow the user to take other appropriate actions, such as eating a meal, taking a particular drug or therapeutic agent, take a rest, etc. functionalized particles/therapeutic agents as well as make other related decisions (e.g., for diabetics to eat a meal or not and what foods should be eaten). The handheld device can also be configured to send a signal to swallowable device 10 to over-ride release 58 or actuator 50 thereby allowing the user to intervene to prevent, delay or accelerate the delivery of functionalized particles, based upon other symptoms and/or patient actions (e.g., eating a meal, deciding to go to sleep, exercise etc.). The user may also externally trigger release 58 or activate actuator 60 at a selected time period after swallowing the capsule. The time period can be correlated to a typical transit time or range of transit times for food moving through the user's GI tract to a particular location in the tract such as the small intestine.

Other embodiments and configurations of a device for delivering functionalized particles to the intestinal tract are also contemplated. For example, other swallowable capsule-like delivery devices may also be used herein. Swallowable capsules may utilize certain enteric, protective or sustained-release coatings, such as Eudragit®, which can be configured to dissolve in the intestines, but not in low pH environment of the stomach. Embodiments of device using such coatings or materials may be configured such that the capsule dissolves in the intestine, delivering the functionalized particles to the lumen of the intestine for subsequent diffusion into the tissue and blood.

Once delivered, the functionalized particles may need to cross the epithelial layer of the small intestinal wall either through paracellular or transcellular routes. Because of the tight junctions of the paracellular space in the order of a few nanometers in width, it may be difficult for relatively large functionalized particles, e.g., 100-200 nm nanoparticles, to diffuse around the cells. Therefore, in some embodiments, the functionalized particles can be labeled with active transport ligands used in oral delivery systems for intestinal targeting. Representative ligands include FCRn receptors which can assist in actively transporting the functionalized particles across the epithelial barrier via the FCRn receptor-mediated endocytosis mechanism with exocytosis on the basolateral side of the epithelial cells. FCRn receptors are pH-sensitive binding receptors on the apical side of epithelial cells and are responsible for the transport of IgG in breast milk from mother to infant. Other active transport ligands include vitamin B12, integrin receptors as well as saccharides.

In some examples, the capsules used to deliver the functionalized particles to the intestinal tract can be coated at least in part with a layer of a mucoadhesion material. The mucoadhesive layer can improve delivery of the functionalized particles into the intestinal by promoting binding of the capsule to the intestinal wall in order to increase the retention time of the capsule in the GI tract. An enteric coating placed over the mucoadhesive layer can shield the mucoadhesive layer from degradation by stomach acids and selectively degrade in the intestinal tract, exposing the mucoadhesive layer once the capsule reaches the small intestine. Representative examples of mucoadhesives include cellulose derivatives such as hydroxypropyl methylcellulose, hydroxypropyl cellulose (HPC), methylcellulose (MC) and carboxymethyl cellulose (CMC); insoluble cellulose derivatives such as ethylcellulose and microcrystalline cellulose (MCC); polyacrylates such as Carbopol 971P; starch such as degradable starch microspheres (DSM); and chitosan and its derivatives.

Figure 12A:
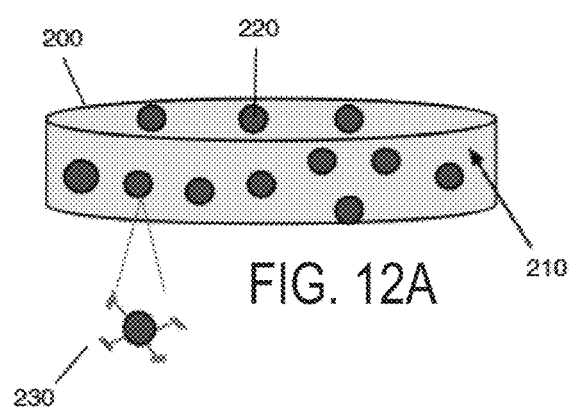
FIGS. 12A-12C are perspective views of the preparation of a swallowable pellet.
Figure 12B:
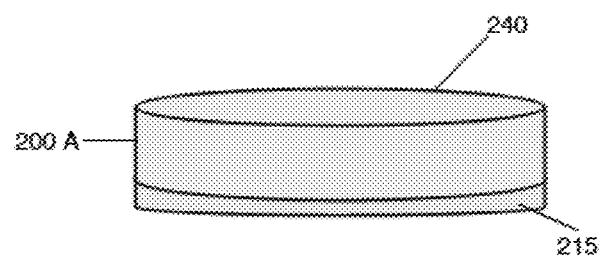
Figure 12C:
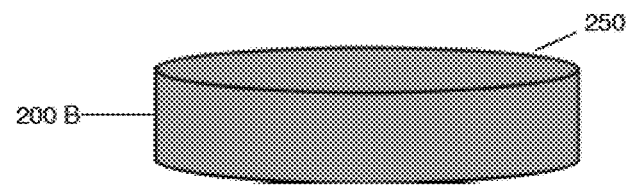

In an alternative embodiment, a composition is provided for oral administration without any need for a capsule, tissue penetrating members, etc. The composition includes a core comprising a mucoadhesive material and at least one type of functionalized particles, wherein the least one type of functionalized particles is labeled with an active transport ligand and wherein the mucoadhesive material is configured to adhere to a wall of the gastrointestinal tract; excipient surrounding at least a portion of the core; and an enteric coating surrounding the excipient and the core, wherein the enteric coating configured to protect the core from stomach acid while allowing for degradation of the core in a target portion of the gastrointestinal tract. The composition includes an active transport ligand, e.g., FCRn receptor, labeled functionalized particles encapsulated in a swallowable pellet. Such functionalized particles 220 labeled with an active transport ligand, e.g., FCRn receptor 230, can be mixed with mucoadhesive material 210 and compressed to form a core 200 as shown in FIG. 12A. In some embodiments, the core is planar. The planar geometry of the core can assist in withstanding the shear flow of GI mucus and increasing residence time. Generally, the ratio of functionalized particles to mucoadhesive material ranges from 10:90 to 40:60. The planar core 200 can then be partially coated with a non-mucoadhesive material such as an excipient 240, e.g., ethyl cellulose, such that one mucoadhesive side 215 is exposed for preferential mucoadhesive attachment and for generating a unidirectional concentration gradient of the functionalized particles across the gut wall. See FIG. 12B. An enteric coating 250 is then placed over the partially coated planar core 200A to form a coated pellet 200B which is configured for direct oral administration. See FIG. 12C. The thickness of the enteric coating can range from 100 um to 500 uM, generally around 100 um to 200 um.

IV. Example Systems

Figure 13:
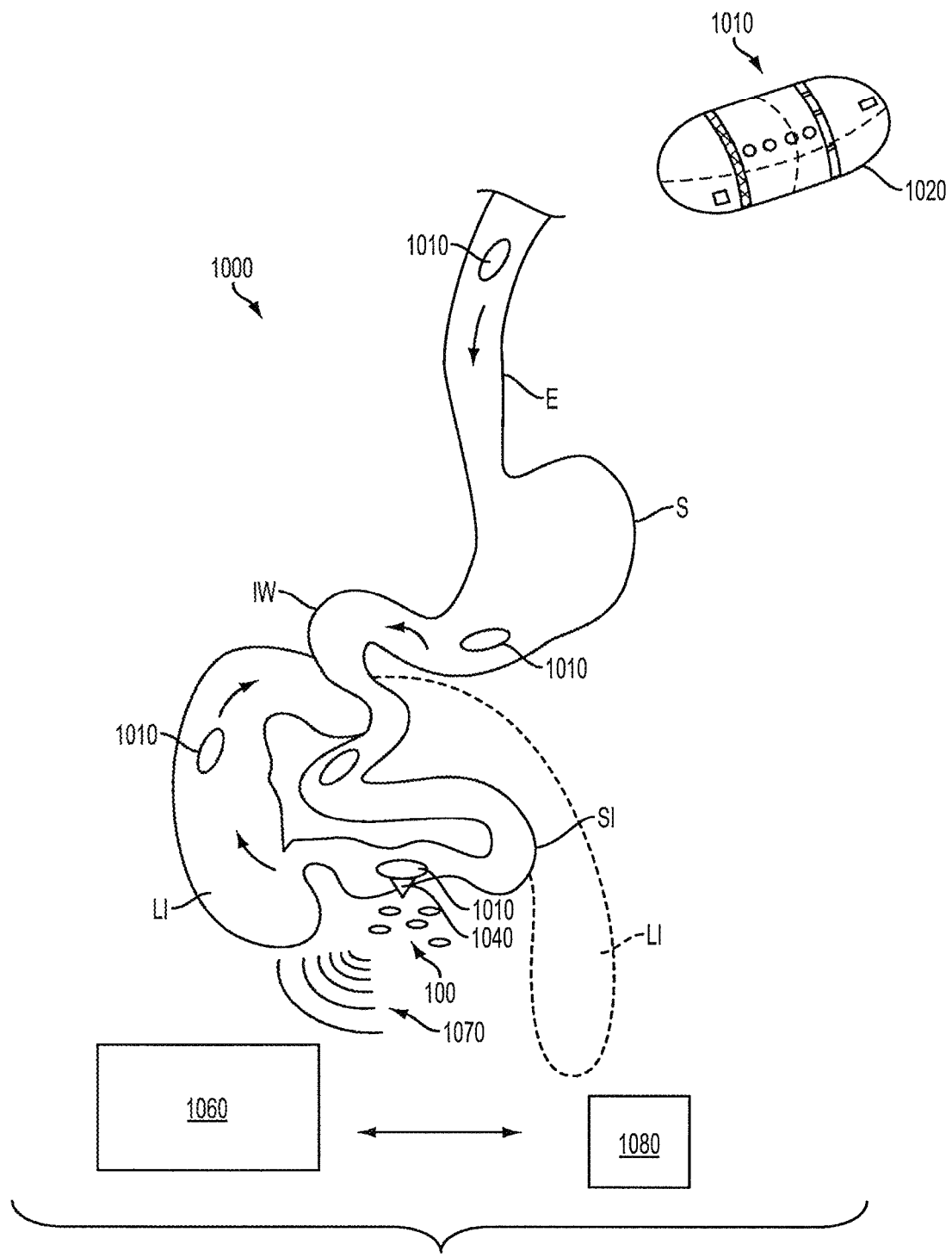
FIG. 13 is a view of an embodiment of a system including a swallowable delivery device.

A system 1000, including a swallowable device 1010 comprising a capsule 1020, at least one tissue penetrating member 1040, and an actuator 1050 (not shown), as shown in FIG. 13, may also be provided. Swallowable device 1010 may include any embodiments of the swallowable devices described above. The system may further include a plurality of functionalized particles 100 configured to interact with one or more target analytes present in blood in a lumen of the subsurface vasculature, disposed within a capsule 1020 of the device 1010. The plurality of physiological parameters obtained by the functionalized particles 100 delivered by an embodiment of the swallowable device 1010 may be measured by a detector 1060 configured to detect an analyte response signal 1070 transmitted from the portion of subsurface vasculature. The analyte response signal 1070 may be related to the interaction of the one or more target analytes to the functionalized particles 100. In further embodiments, the system 1000 may also include a processor 1080 configured to detect the presence or absence of the clinically-relevant analyte based, at least in part, on the analyte response signal 1070. The processor 1080 may also be configured, in other examples, to determine a concentration of the clinically-relevant analyte based, at least in part, on the analyte response signal 1070. The detector 1060 may be located internal or external to the body of the patient and may be provided on a single platform with the processor 1080. In other examples, the processor 1080 may be remote from the detector 1060.

Figure 14:
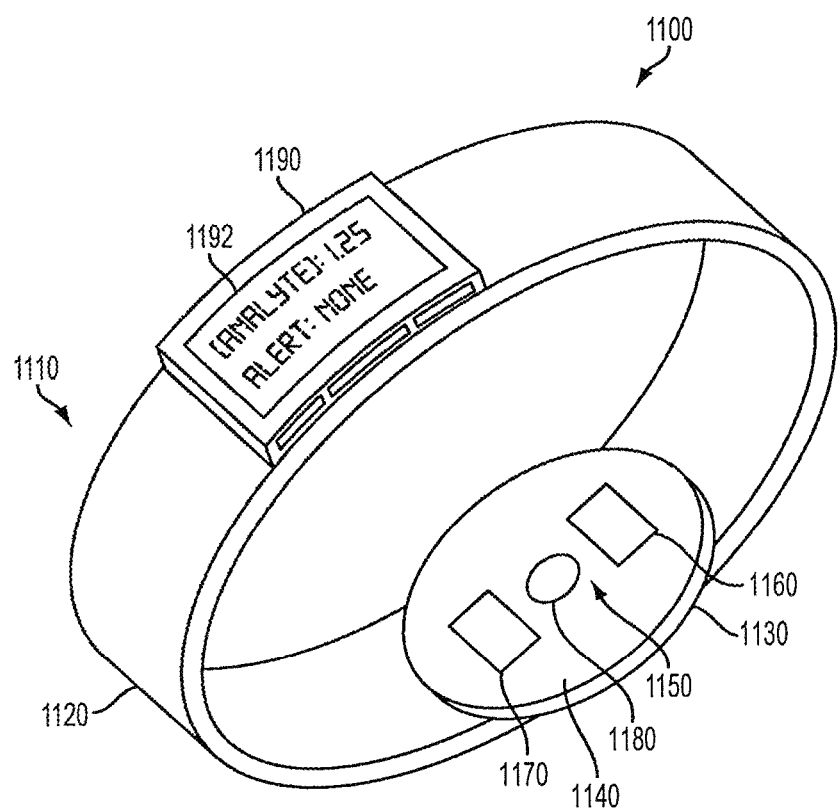
FIG. 14 is a perspective view of an example wearable device for detecting and measuring a plurality of physiological parameters.

In some examples, the detector may be mounted on a wearable device 1100 configured to automatically measure a plurality of physiological parameters of a person wearing the device. The term "wearable device," as used in this disclosure, refers to any device that is capable of being worn at, on or in proximity to a body surface, such as a wrist, ankle, waist, chest, or other body part. In order to take in vivo measurements in a noninvasive manner from outside of the body, the wearable device may be positioned on a portion of the body where subsurface vasculature is easily observable, the qualification of which will depend on the type of detection system used. The device may be placed in close proximity to the skin or tissue, but need not be touching or in intimate contact therewith. A mount 1110, such as a belt, wristband, ankle band, etc. can be provided to mount the device at, on or in proximity to the body surface. The mount 1110 may prevent the wearable device from moving relative to the body to reduce measurement error and noise. In one example, shown in FIG. 14, the mount 1110, may take the form of a strap or band 120 that can be worn around a part of the body. Further, the mount 1110 may be an adhesive substrate for adhering the wearable device 1100 to the body of a wearer.

A measurement platform 1130 is disposed on the mount 1110 such that it can be positioned on the body where subsurface vasculature is easily observable. An inner face 1140 of the measurement platform is intended to be mounted facing to the body surface. The measurement platform 1130 may house the data collection system 1150, which may include at least one detector 1160 for detecting at least one physiological parameter, which could include any parameters that may relate to the health of the person wearing the wearable device. For example, the detector 1160 could be configured to measure blood pressure, pulse rate, respiration rate, skin temperature, etc. At least one of the detectors 1160 is configured to noninvasively measure one or more analytes in blood circulating in subsurface vasculature proximate to the wearable device. In a non-exhaustive list, detector 1160 may include any one of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor. The components of the data collection system 150 may be miniaturized so that the wearable device may be worn on the body without significantly interfering with the wearer's usual activities.

In some examples, the data collection system 1150 further includes a signal source 1170 for transmitting an interrogating signal that can penetrate the wearer's skin into the portion of subsurface vasculature, for example, into a lumen of the subsurface vasculature. The interrogating signal can be any kind of signal that is benign to the wearer, such as electromagnetic, magnetic, optic, acoustic, thermal, mechanical, and results in a response signal that can be used to measure a physiological parameter or, more particularly, that can detect the binding of the clinically-relevant analyte to the functionalized particles. In one example, the interrogating signal is an electromagnetic pulse (e.g., a radio frequency (RF) pulse) and the response signal is a magnetic resonance signal, such as nuclear magnetic resonance (NMR). In another example, the interrogating signal is a time-varying magnetic field, and the response signal is an externally-detectable physical motion due to the time-varying magnetic field. The time-varying magnetic field modulates the particles by physical motion in a manner different from the background, making them easier to detect. In a further example, the interrogating signal is an electromagnetic radiation signal. In particular, the interrogating signal may be electromagnetic radiation having a wavelength between about 400 nanometers and about 1600 nanometers. The interrogating signal may, more particularly, comprise electromagnetic radiation having a wavelength between about 500 nanometers and about 1000 nanometers. In some examples, the functionalized particles include a fluorophore. The interrogating signal may therefore be an electromagnetic radiation signal with a wavelength that can excite the fluorophore and penetrate the skin or other tissue and subsurface vasculature (e.g., a wavelength in the range of about 500 to about 1000 nanometers), and the response signal is fluorescence radiation from the fluorophore that can penetrate the subsurface vasculature and tissue to reach the detector.

In some cases, an interrogating signal is not necessary to measure one or more of the physiological parameters and, therefore, the wearable device 1100 may not include a signal source 1170. For example, the functionalized particles may include an autofluorescent or luminescent marker, such as a fluorophore, that will automatically emit a response signal indicative of the binding of the clinically-relevant analyte to the functionalized particles, without the need for an interrogating signal or other external stimulus. In some examples, the functionalized particles may include a chemiluminescent marker configured to produce a response signal in the form of fluorescence radiation produced in response to a chemical reaction initiated, at least in part, to the binding of the target analyte to the particle.

A collection magnet 1180 may also be included in the data collection system 1150. In such embodiments, the functionalized particles may also be made of or be functionalized with magnetic materials, such as ferromagnetic, paramagnetic, super-paramagnetic, or any other material that responds to a magnetic field. The collection magnet 180 is configured to direct a magnetic field into the portion of subsurface vasculature that is sufficient to cause functionalized magnetic particles to collect in a lumen of that portion of subsurface vasculature. The magnet may be an electromagnet that may be turned on during measurement periods and turned off when a measurement period is complete so as to allow the magnetic particles to disperse through the vasculature.

The wearable device 1100 may also include a user interface 1190 via which the wearer of the device may receive one or more recommendations or alerts generated either from a remote server or other remote computing device, or from a processor within the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the user interface 1190 may include a display 1192 where a visual indication of the alert or recommendation may be displayed. The display 1192 may further be configured to provide an indication of the measured physiological parameters, for instance, the concentrations of certain blood analytes being measured.

Figure 15A:
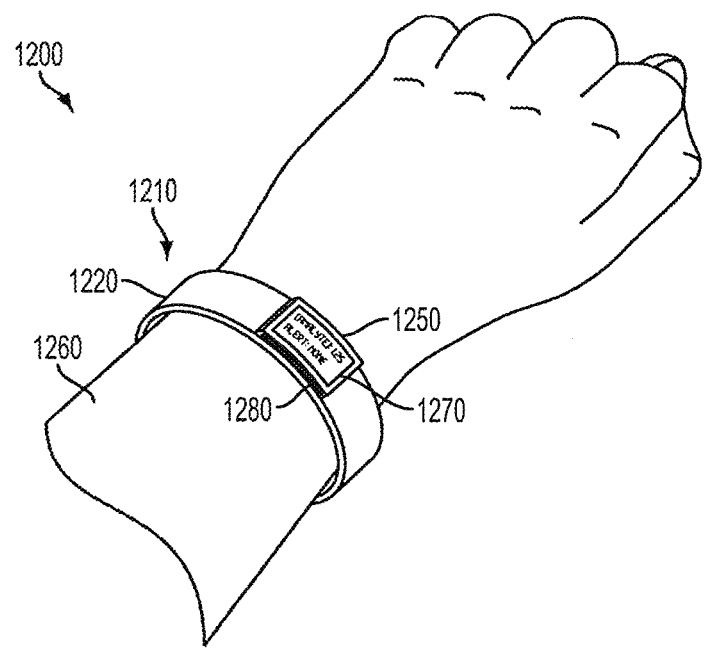
FIG. 15A is a perspective top view of an example wrist-mounted device, when mounted on a wearer's wrist.
Figure 15B:
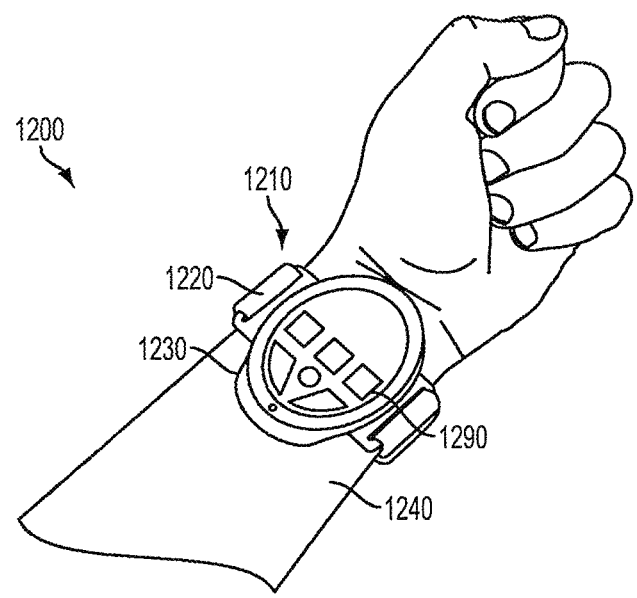
FIG. 15B is a perspective bottom view of an example wrist-mounted device shown in FIG. 15A, when mounted on a wearer's wrist.

In one example, the wearable device is provided as a wrist-mounted device 1200, as shown in FIGS. 15A and 15B. The wrist-mounted device may be mounted to the wrist of a living subject with a wristband or cuff, similar to a watch or bracelet. As shown in FIGS. 2A and 2B, the wrist mounted device 1200 may include a mount 1210 in the form of a wristband 1220, a measurement platform 1230 positioned on the anterior side 1240 of the wearer's wrist, and a user interface 1250 positioned on the posterior side 1260 of the wearer's wrist. The wearer of the device may receive, via the user interface 1250, one or more recommendations or alerts generated either from a remote server or other remote computing device, or alerts from the measurement platform. Such a configuration may be perceived as natural for the wearer of the device in that it is common for the posterior side 1260 of the wrist to be observed, such as the act of checking a wrist-watch. Accordingly, the wearer may easily view a display 1270 on the user interface. Further, the measurement platform 1230 may be located on the anterior side 1240 of the wearer's wrist where the subsurface vasculature may be readily observable. However, other configurations are contemplated.

The display 1270 may be configured to display a visual indication of the alert or recommendation and/or an indication of the measured physiological parameters, for instance, the concentrations of certain blood analytes being measured. Further, the user interface 1250 may include one or more buttons 1280 for accepting inputs from the wearer. For example, the buttons 1280 may be configured to change the text or other information visible on the display 270. As shown in FIG. 15B, measurement platform 1230 may also include one or more buttons 1290 for accepting inputs from the wearer. The buttons 1290 may be configured to accept inputs for controlling aspects of the data collection system, such as initiating a measurement period, or inputs indicating the wearer's current health state (i.e., normal, migraine, shortness of breath, heart attack, fever, "flu-like" symptoms, food poisoning, etc.).

In other examples of wrist-mounted device, the measurement platform and user interface may both be provided on the same side of the wearer's wrist, in particular, the anterior side of the wrist. The wrist mounted device may also be provided with a watch face on the posterior side of the wearer's wrist.

Figure 16:
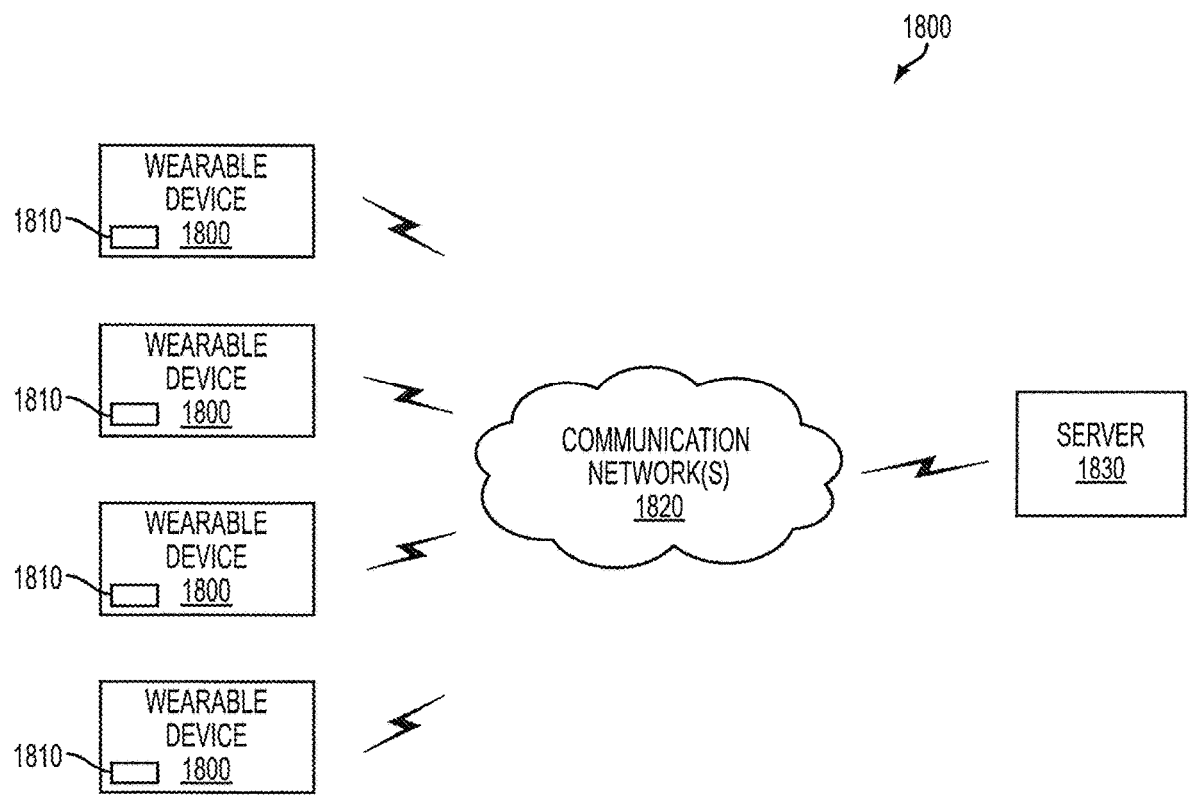
FIG. 16 is a block diagram of an example system that includes a plurality of wrist mounted devices in communication with a server.

FIG. 16 is a simplified schematic of a system including one or more wearable devices 1800. The one or more wearable devices 700 may be configured to transmit data via a communication interface 1810 over one or more communication networks 1820 to a remote server 1830. In one embodiment, the communication interface 1810 includes a wireless transceiver for sending and receiving communications to and from the server 1830. In further embodiments, the communication interface 1810 may include any means for the transfer of data, including both wired and wireless communications. For example, the communication interface may include a universal serial bus (USB) interface or a secure digital (SD) card interface. Communication networks 1820 may be any one of may be one of: a plain old telephone service (POTS) network, a cellular network, a fiber network and a data network. The server 1830 may include any type of remote computing device or remote cloud computing network. Further, communication network 1820 may include one or more intermediaries, including, for example wherein the wearable device 1800 transmits data to a mobile phone or other personal computing device, which in turn transmits the data to the server 1830.

In addition to receiving communications from the wearable device 1800, such as collected physiological parameter data and data regarding health state as input by the user, the server may also be configured to gather and/or receive either from the wearable device 1800 or from some other source, information regarding a wearer's overall medical history, environmental factors and geographical data. For example, a user account may be established on the server for every wearer that contains the wearer's medical history. Moreover, in some examples, the server 1830 may be configured to regularly receive information from sources of environmental data, such as viral illness or food poisoning outbreak data from the Centers for Disease Control (CDC) and weather, pollution and allergen data from the National Weather Service. Further, the server may be configured to receive data regarding a wearer's health state from a hospital or physician. Such information may be used in the server's decision-making process, such as recognizing correlations and in generating clinical protocols.

Additionally, the server may be configured to gather and/or receive the date, time of day and geographical location of each wearer of the device during each measurement period. Such information may be used to detect and monitor spatial and temporal spreading of diseases. As such, the wearable device may be configured to determine and/or provide an indication of its own location. For example, a wearable device may include a GPS system so that it can include GPS location information (e.g., GPS coordinates) in a communication to the server. As another example, a wearable device may use a technique that involves triangulation (e.g., between base stations in a cellular network) to determine its location. Other location-determination techniques are also possible.

The server may also be configured to make determinations regarding the efficacy of a drug or other treatment based on information regarding the drugs or other treatments received by a wearer of the device and, at least in part, the physiological parameter data and the indicated health state of the user. From this information, the server may be configured to derive an indication of the effectiveness of the drug or treatment. For example, if a drug is intended to treat nausea and the wearer of the device does not indicate that he or she is experiencing nausea after beginning a course of treatment with the drug, the server may be configured to derive an indication that the drug is effective for that wearer. In another example, a wearable device may be configured to measure blood glucose. If a wearer is prescribed a drug intended to treat diabetes, but the server receives data from the wearable device indicating that the wearer's blood glucose has been increasing over a certain number of measurement periods, the server may be configured to derive an indication that the drug is not effective for its intended purpose for this wearer.

Further, some embodiments of the system may include privacy controls which may be automatically implemented or controlled by the wearer of the device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

IV. Illustrative Methods

Figure 17:
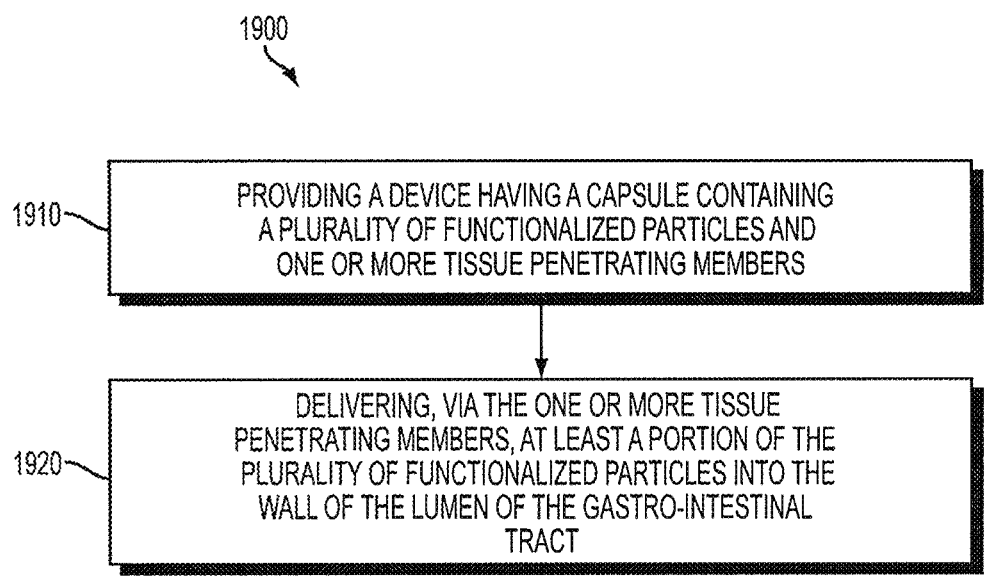
FIG. 17 is a block diagram of an example method of delivering functionalized particles.

FIG. 17 is a flowchart of a method 1900 for delivering functionalized particles to the body. A swallowable device having: (1) a capsule containing a plurality of functionalized particles, and (2) a plurality of tissue penetrating members is first ingested (1910). The capsule is sized to pass through a lumen of a gastrointestinal tract. Each of the tissue penetrating members has a lumen and an exit through which the functionalized particles can pass. Alternatively, the tissue penetrating members are solid and encapsulate the functionalized particles either in the polymer matrix of the penetrating members or in a space within the penetrating members (not shown). The tissue penetrating members are further configured to puncture a wall of the lumen of a target portion of the gastrointestinal tract. The target portion of the gastrointestinal tract could be the small intestine, large intestine, stomach, etc. At least a portion of the plurality of functionalized particles are delivered via the plurality of tissue penetrating members into the wall of the lumen of the target portion of the gastrointestinal tract (1920). Delivery of the functionalized particles may occur in response to a chemical condition in the target portion of the gastrointestinal tract. For example, delivery may occur upon exposure to chemical conditions in the small or large intestine such as pH, such as upon exposure to a selected pH in the small intestine, e.g., 7.0, 7.1, 7.2, 7.3, 7.4, 7.5, 7.6 8.0 or greater. In some examples, delivery may occur in a pH range from 7.0 to 7.5. In other examples, delivery may occur in response to a mechanical or electrochemical stimulus. In still further examples, delivery may occur in response to a stimulus remote from the swallowable device.

In another example method, a plurality of functionalized particles is loaded into a device having a capsule sized to pass through a lumen of a gastrointestinal tract, the plurality of tissue penetrating members, and an actuator having a first configuration and a second configuration. The plurality of functionalized particles may be loaded into the capsule such that they are communication with the plurality of tissue penetrating members. The tissue penetrating members may be configured to puncture a wall of the lumen of a target portion of the gastrointestinal tract and each may have a respective penetrating-member exit. The actuator is configured to retain the plurality of tissue penetrating members within the capsule in the first configuration. Further, by transitioning from the first configuration to the second configuration, the actuator is configured to advance the plurality of tissue penetrating members from the capsule into a wall of the lumen of the target portion of the gastrointestinal tract. At least a portion of the functionalized particles may be delivered into the wall of the lumen of the target portion of the gastrointestinal tract by the actuator transitioning from the first configuration to the second configuration. The actuator may be configured to transition from the first configuration to the second configuration in response to a chemical condition in the target portion of the gastrointestinal tract, such as a predetermined pH value, in response to a mechanical input, or in response to an input remote from the device.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

V. Conclusion

The particular arrangements shown in the figures should not be viewed as limiting. It should be understood that other embodiments can include more or less of each element shown in a given figure. Further, some of the illustrated elements can be combined or omitted. Yet further, an example embodiment can include elements that are not illustrated in the figures.

It will be readily understood that the aspects of the present disclosure, as generally described herein, and illustrated in the figures, can be arranged, substituted, combined, separated, and designed in a wide variety of different configurations, all of which are explicitly contemplated herein. While various aspects and embodiments have been disclosed herein, other aspects and embodiments will be apparent to those skilled in the art.

Example methods and systems are described above. It should be understood that the words "example" and "exemplary" are used herein to mean "serving as an example, instance, or illustration." Any embodiment or feature described herein as being an "example" or "exemplary" is not necessarily to be construed as preferred or advantageous over other embodiments or features. Reference is made herein to the accompanying figures, which form a part thereof. In the figures, similar symbols typically identify similar components, unless context dictates otherwise. Other embodiments may be utilized, and other changes may be made, without departing from the spirit or scope of the subject matter presented herein. The various aspects and embodiments disclosed herein are for purposes of illustration and are not intended to be limiting, with the true scope and spirit being indicated by the following claims.

Where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

What is claimed is:

1. A device comprising:
a capsule sized to pass through a lumen of a gastrointestinal tract; an enteric coating surrounding at least a portion of the capsule, the enteric coating configured to protect the capsule from stomach acid while allowing for degradation of the capsule in a target portion of the gastrointestinal tract;
a plurality of tissue penetrating members arranged within the capsule and configured to puncture a wall of the lumen of the target portion of the gastrointestinal tract, the tissue penetrating members comprising at least one type of functionalized particles; and
an actuator having a first configuration and a second configuration, wherein the actuator is configured to retain the plurality of tissue penetrating members within the capsule in the first configuration, wherein the actuator is configured to advance the at least one type of functionalized particles into or across a wall of the lumen of the target portion of the gastrointestinal tract via the plurality of tissue penetrating members by the actuator transitioning from the first configuration to the second configuration, wherein the actuator comprises an expandable polymer configured to expand after the capsule arrives at the target portion of the gastrointestinal tract,
wherein the actuator is not a balloon;
wherein the expandable polymer is a pH-triggered expandable polymer,
wherein the plurality of tissue penetrating members is around the expandable polymer, and
wherein the expandable polymer is configured to advance the plurality of tissue penetrating members.

2. The device of claim 1, further comprising a mucoadhesion layer between the enteric coating and the capsule, the mucoadhesion layer configured to attach the capsule to a wall of the target portion of the gastrointestinal tract.

3. The device of claim 1, wherein each of the plurality of tissue penetrating members comprises a respective penetrating-member lumen and respective penetrating-member exit through which the functionalized particles can pass.

4. The device of claim 3, wherein each of the plurality of tissue penetrating members further comprises a respective delivery member coupled to the actuator and configured to advance the functionalized particles through the respective penetrating-member lumen toward the respective penetrating-member exit.

5. The device of claim 1, wherein the functionalized particles include a receptor having an affinity for a target analyte.

6. The device of claim 5, wherein the receptor is chosen from the group consisting of antibodies, nucleic acids, low molecular weight ligands, peptides, proteins, polysaccharides, polyunsaturated fatty acids, plasmids, viruses and phages.

7. The device of claim 1, wherein the functionalized particles include one or more of a fluorescent, an autofluorescent, a luminescent and a chemiluminescent marker.

8. The device of claim 1, wherein the functionalized particles include a paramagnetic, super-paramagnetic or ferromagnetic material.

9. The device of claim 1, wherein the functionalized particles are formed from a biodegradable material.

10. A device comprising:
a capsule sized to pass through a lumen of a gastrointestinal tract;
an enteric coating surrounding at least a portion of the capsule;
a plurality of tissue penetrating members arranged within the capsule, the tissue penetrating members comprising at least one type of functionalized particles; and
an actuator configured to advance the tissue penetrating members into a wall of the lumen of a target portion of the gastrointestinal tract,
wherein the actuator comprises an expandable polymer configured to expand after the capsule arrives at the target portion of the gastrointestinal tract,
wherein the actuator is not a balloon,
wherein the expandable polymer is a pH-triggered expandable polymer, wherein the plurality of tissue penetrating members is around the expandable polymer, and wherein the expandable polymer is configured to advance the plurality of tissue penetrating members.

* * * * *